(12) United States Patent  (10) Patent No.: US 7,951,173 B2
Hammill, Sr. et al.  (45) Date of Patent: May 31, 2011

(54) PEDICLE SCREW IMPLANT SYSTEM

(75) Inventors: John E. Hammill, Sr., Maumee, OH (US); Robert L. Doubler, Monroe, MI (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 0 days.

(21) Appl. No.: 12/700,436

(22) Filed: Feb. 4, 2010

(65) Prior Publication Data

US 2010/0137920 A1  Jun. 3, 2010

Related U.S. Application Data

(63) Continuation-in-part of application No. 12/540,398, filed on Aug. 13, 2009, which is a continuation-in-part of application No. 11/749,615, filed on May 16, 2007, and a continuation-in-part of application No. 12/355,145, filed on Jan. 16, 2009.

(51) Int. Cl.
*A61B 17/70* (2006.01)

(52) U.S. Cl. .................. 606/269; 606/267; 606/308

(58) Field of Classification Search .................. 606/246, 606/265, 279, 305–309
See application file for complete search history.

(56) References Cited

U.S. PATENT DOCUMENTS

| 3,433,510 A | 3/1969 | Hulterstrum |
| 4,273,116 A | 6/1981 | Chiquet |
| 4,419,026 A | 12/1983 | Leto |
| 4,483,334 A | 11/1984 | Murray |
| 4,570,982 A | 2/1986 | Blose et al. |
| 4,693,240 A | 9/1987 | Evans |
| 4,708,510 A | 11/1987 | McConnell et al. |
| 4,763,644 A | 8/1988 | Webb |
| 4,805,602 A | 2/1989 | Puno et al. |
| 4,836,196 A | 6/1989 | Park et al. |
| 4,841,959 A | 6/1989 | Ransford |
| 4,854,304 A | 8/1989 | Zielke |
| 4,867,144 A | 9/1989 | Karas et al. |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,005,562 A | 4/1991 | Cotrel |
| 5,084,049 A | 1/1992 | Asher et al. |

(Continued)

FOREIGN PATENT DOCUMENTS

DE  G9202745.8  4/1992

(Continued)

*Primary Examiner* — Thomas C Barrett
*Assistant Examiner* — Michael J Araj
(74) *Attorney, Agent, or Firm* — McHale & Slavin, P.A.

(57) ABSTRACT

A pedicle screw fastening that can be made polyaxial, monoaxial, fixed, or provide a predefined monoaxial placement. The fastening system consists of an anchoring bone screw having threads on one end for use in anchoring to the screw to the spine and a spherical connector on the other end operating as a pivot point about which a U-shaped or side loading connecting assembly is used to secure to a connecting rod for use in stabilization of a spine. The connecting assembly, for receipt of a spinal connecting rod, includes a biased retainer ring for maintaining a positive tension between the connecting assembly and the anchored screw. The system allows for an improved manufacturing step wherein the threaded shank of a bone screws can be passed through a lower portion of the connecting assembly allowing a variety of bone screw sizes to be used with a common sized connector.

30 Claims, 16 Drawing Sheets

U.S. PATENT DOCUMENTS

| | | |
|---|---|---|
| 5,085,660 A | 2/1992 | Lin |
| 5,092,893 A | 3/1992 | Smith |
| 5,129,388 A | 7/1992 | Vignaud et al. |
| 5,129,900 A | 7/1992 | Asher et al. |
| 5,133,716 A | 7/1992 | Plaza |
| 5,133,717 A | 7/1992 | Chopin |
| 5,176,678 A | 1/1993 | Tsou |
| 5,207,678 A | 5/1993 | Harms et al. |
| 5,217,497 A | 6/1993 | Mehdian |
| 5,257,993 A | 11/1993 | Asher et al. |
| 5,261,909 A | 11/1993 | Sutterlin et al. |
| 5,261,912 A | 11/1993 | Frigg |
| 5,312,404 A | 5/1994 | Asher et al. |
| 5,312,405 A | 5/1994 | Korotko et al. |
| 5,330,477 A | 7/1994 | Crook |
| 5,360,431 A | 11/1994 | Puno et al. |
| 5,364,399 A | 11/1994 | Lowery et al. |
| 5,395,371 A | 3/1995 | Miller et al. |
| 5,429,639 A | 7/1995 | Judet |
| 5,437,671 A | 8/1995 | Lozier et al. |
| 5,443,467 A | 8/1995 | Biedermann et al. |
| 5,466,237 A | 11/1995 | Byrd, III et al. |
| 5,470,333 A | 11/1995 | Ray |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,496,321 A | 3/1996 | Puno et al. |
| 5,498,262 A | 3/1996 | Bryan |
| 5,498,263 A | 3/1996 | DiNello et al. |
| 5,501,684 A | 3/1996 | Schlapfer et al. |
| 5,520,690 A | 5/1996 | Errico et al. |
| 5,527,314 A | 6/1996 | Brumfield et al. |
| 5,531,746 A | 7/1996 | Errico et al. |
| 5,545,164 A | 8/1996 | Howland |
| 5,549,608 A | 8/1996 | Errico et al. |
| 5,554,157 A | 9/1996 | Errico et al. |
| 5,562,661 A | 10/1996 | Yoshimi et al. |
| 5,569,247 A | 10/1996 | Morrison |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,165 A | 1/1997 | Jackson |
| 5,591,166 A | 1/1997 | Bernhardt et al. |
| 5,601,552 A | 2/1997 | Cotrel |
| 5,601,553 A | 2/1997 | Trebing et al. |
| 5,607,426 A | 3/1997 | Ralph et al. |
| 5,609,593 A | 3/1997 | Errico et al. |
| 5,609,594 A | 3/1997 | Errico et al. |
| 5,628,740 A | 5/1997 | Mullane |
| 5,643,261 A | 7/1997 | Schafer et al. |
| 5,643,265 A | 7/1997 | Errico et al. |
| 5,647,873 A | 7/1997 | Errico et al. |
| 5,669,910 A | 9/1997 | Korhonen et al. |
| 5,669,911 A | 9/1997 | Errico et al. |
| 5,672,176 A | 9/1997 | Biedermann et al. |
| 5,681,319 A | 10/1997 | Biedermann et al. |
| 5,688,272 A | 11/1997 | Montague et al. |
| 5,688,273 A | 11/1997 | Errico et al. |
| 5,690,630 A | 11/1997 | Errico et al. |
| 5,716,355 A | 2/1998 | Jackson et al. |
| 5,716,356 A | 2/1998 | Biedermann et al. |
| 5,716,357 A | 2/1998 | Rogozinski |
| 5,725,528 A | 3/1998 | Errico et al. |
| 5,725,588 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,810,818 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,947,966 A | 9/1999 | Drewry et al. |
| 5,954,725 A | 9/1999 | Sherman et al. |
| 5,961,517 A | 10/1999 | Biedermann et al. |
| 5,964,760 A | 10/1999 | Richelsoph |
| 5,980,523 A | 11/1999 | Jackson |
| 6,010,503 A | 1/2000 | Richelsoph et al. |
| 6,015,409 A | 1/2000 | Jackson |
| 6,019,759 A | 2/2000 | Rogozinski |
| 6,022,350 A | 2/2000 | Ganem |
| 6,050,997 A | 4/2000 | Mullane |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,080,156 A | 6/2000 | Asher et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,600 A | 9/2000 | Drummond et al. |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,187,005 B1 | 2/2001 | Brace et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,261,287 B1 | 7/2001 | Metz-Stavenhagen |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,383,190 B1 | 5/2002 | Preissman |
| 6,402,752 B2 | 6/2002 | Schaffler-Wachter et al. |
| 6,436,100 B1 | 8/2002 | Berger |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,537,276 B2 | 3/2003 | Metz-Stavenhagen |
| 6,547,789 B1 | 4/2003 | Ventre et al. |
| 6,547,790 B2 | 4/2003 | Harkey, III et al. |
| 6,551,320 B2 | 4/2003 | Liebermann |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |

| Patent No. | Date | Name |
|---|---|---|
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,641,586 B2 | 11/2003 | Varieur |
| 6,648,885 B1 | 11/2003 | Friesem |
| 6,648,887 B2 | 11/2003 | Ashman |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,672,788 B2 | 1/2004 | Hathaway |
| 6,673,073 B1 | 1/2004 | Schafer |
| 6,676,661 B1 | 1/2004 | Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | St. Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,830 B2 | 6/2004 | Minfelde et al. |
| 6,755,835 B2 | 6/2004 | Schultheiss et al. |
| 6,755,836 B1 | 6/2004 | Lewis |
| 6,761,723 B2 | 7/2004 | Butterman et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,905,500 B2 | 6/2005 | Jeon et al. |
| 6,932,817 B2 | 8/2005 | Baynham et al. |
| 6,945,972 B2 | 9/2005 | Frigg et al. |
| 6,951,561 B2 | 10/2005 | Warren et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| RE39,089 E | 5/2006 | Ralph et al. |
| 7,066,937 B2 | 6/2006 | Shluzas |
| 7,087,057 B2 | 8/2006 | Konieczynski et al. |
| 7,128,743 B2 | 10/2006 | Metz-Stavenhagen |
| 7,144,396 B2 | 12/2006 | Shluzas |
| 7,163,538 B2 | 1/2007 | Altarac et al. |
| 7,223,268 B2 | 5/2007 | Biedermann |
| 7,306,606 B2 | 12/2007 | Sasing |
| 7,322,981 B2 | 1/2008 | Jackson |
| 7,335,202 B2 | 2/2008 | Matthis et al. |
| 7,445,627 B2 | 11/2008 | Hawkes et al. |
| 7,604,656 B2 | 10/2009 | Shluzas |
| 7,682,377 B2 | 3/2010 | Konieczynski |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0082602 A1 | 6/2002 | Biedermann et al. |
| 2002/0103487 A1 | 8/2002 | Errico et al. |
| 2002/0111626 A1 | 8/2002 | Ralph et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0004512 A1 | 1/2003 | Farris |
| 2003/0023243 A1 | 1/2003 | Biedermann et al. |
| 2003/0045879 A1 | 3/2003 | Minfelde et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0118395 A1 | 6/2003 | Abels et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0024464 A1 | 2/2004 | Errico et al. |
| 2004/0092934 A1 | 5/2004 | Howland |
| 2004/0097933 A1 | 5/2004 | Lourdel et al. |
| 2004/0102781 A1 | 5/2004 | Jeon |
| 2004/0116929 A1 | 6/2004 | Barker et al. |
| 2004/0127906 A1 | 7/2004 | Culbert et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0181224 A1 | 9/2004 | Biedermann |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0033289 A1 | 2/2005 | Warren et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131409 A1 | 6/2005 | Chervitz et al. |
| 2005/0131413 A1 | 6/2005 | O'Driscoll et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192571 A1 | 9/2005 | Abdelgany |
| 2005/0192580 A1 | 9/2005 | Dalton |
| 2005/0203515 A1 | 9/2005 | Doherty et al. |
| 2005/0203516 A1 | 9/2005 | Biedermann et al. |
| 2005/0216003 A1 | 9/2005 | Biedermann et al. |
| 2005/0228392 A1 | 10/2005 | Keyer et al. |

| | | | |
|---|---|---|---|
| 2005/0228501 A1 | 10/2005 | Miller et al. | |
| 2005/0234450 A1 | 10/2005 | Barker | |
| 2005/0234451 A1 | 10/2005 | Markworth | |
| 2005/0234452 A1 | 10/2005 | Malandain | |
| 2005/0240181 A1 | 10/2005 | Boomer et al. | |
| 2005/0240183 A1 | 10/2005 | Vaughan | |
| 2005/0251137 A1 | 11/2005 | Ball | |
| 2005/0251141 A1 | 11/2005 | Frigg et al. | |
| 2005/0261687 A1 | 11/2005 | Garamszegi et al. | |
| 2005/0267474 A1 | 12/2005 | Dalton | |
| 2005/0273099 A1 | 12/2005 | Baccelli et al. | |
| 2005/0273101 A1 | 12/2005 | Shumacher | |
| 2005/0277919 A1 | 12/2005 | Slivka et al. | |
| 2005/0277925 A1 | 12/2005 | Mujwid | |
| 2005/0277928 A1 | 12/2005 | Boschert | |
| 2005/0283152 A1 | 12/2005 | Lindemann et al. | |
| 2005/0283157 A1 | 12/2005 | Coates et al. | |
| 2005/0283238 A1 | 12/2005 | Reiley | |
| 2005/0288669 A1 | 12/2005 | Abdou | |
| 2005/0288671 A1 | 12/2005 | Yuan et al. | |
| 2005/0288673 A1 | 12/2005 | Catbagan et al. | |
| 2006/0004357 A1 | 1/2006 | Lee et al. | |
| 2006/0004359 A1 | 1/2006 | Kramer et al. | |
| 2006/0004360 A1 | 1/2006 | Kramer et al. | |
| 2006/0004363 A1 | 1/2006 | Brockmeyer et al. | |
| 2006/0009769 A1 | 1/2006 | Lieberman | |
| 2006/0009770 A1 | 1/2006 | Speirs et al. | |
| 2006/0015104 A1 | 1/2006 | Dalton | |
| 2006/0015105 A1 | 1/2006 | Warren et al. | |
| 2006/0025767 A1 | 2/2006 | Khalili | |
| 2006/0025768 A1 | 2/2006 | Iott et al. | |
| 2006/0025770 A1 | 2/2006 | Schlapfer et al. | |
| 2006/0036242 A1 | 2/2006 | Nilsson et al. | |
| 2006/0036252 A1 | 2/2006 | Baynham et al. | |
| 2006/0052783 A1 | 3/2006 | Dant et al. | |
| 2006/0052784 A1 | 3/2006 | Dant et al. | |
| 2006/0052786 A1 | 3/2006 | Dant et al. | |
| 2006/0058788 A1 | 3/2006 | Hammer et al. | |
| 2006/0074419 A1* | 4/2006 | Taylor et al. | 606/70 |
| 2006/0084981 A1 | 4/2006 | Shluzas | |
| 2006/0149240 A1 | 7/2006 | Jackson | |
| 2006/0149241 A1 | 7/2006 | Richelsoph | |
| 2006/0155277 A1 | 7/2006 | Metz-Stavenhagen | |
| 2006/0235392 A1 | 10/2006 | Hammer et al. | |
| 2006/0241599 A1 | 10/2006 | Konieczynski et al. | |
| 2006/0241600 A1 | 10/2006 | Ensign et al. | |
| 2006/0241603 A1 | 10/2006 | Jackson | |
| 2006/0276791 A1 | 12/2006 | Shluzas | |
| 2007/0055241 A1 | 3/2007 | Matthis et al. | |
| 2007/0093818 A1 | 4/2007 | Biedermann et al. | |
| 2007/0093826 A1 | 4/2007 | Hawkes et al. | |
| 2007/0118132 A1 | 5/2007 | Culbert et al. | |
| 2007/0123868 A1 | 5/2007 | Culbert et al. | |
| 2007/0161996 A1 | 7/2007 | Biedermann et al. | |
| 2007/0161999 A1 | 7/2007 | Biedermann et al. | |
| 2007/0219556 A1 | 9/2007 | Altarac et al. | |
| 2007/0225712 A1 | 9/2007 | Altarac et al. | |
| 2007/0225713 A1 | 9/2007 | Altarac et al. | |
| 2007/0270813 A1 | 11/2007 | Garamszegi et al. | |
| 2008/0009862 A1 | 1/2008 | Hoffman | |
| 2008/0015576 A1 | 1/2008 | Whipple | |
| 2008/0015579 A1 | 1/2008 | Whipple | |
| 2008/0015580 A1 | 1/2008 | Chao | |
| 2008/0015597 A1 | 1/2008 | Whipple | |
| 2008/0045953 A1 | 2/2008 | Garamszegi | |
| 2008/0097436 A1 | 4/2008 | Culbert et al. | |
| 2008/0177322 A1 | 7/2008 | Davis et al. | |
| 2008/0269809 A1 | 10/2008 | Garamszegi | |
| 2008/0287998 A1 | 11/2008 | Doubler et al. | |
| 2009/0163956 A1 | 6/2009 | Biedermann et al. | |
| 2010/0023061 A1* | 1/2010 | Randol et al. | 606/278 |

FOREIGN PATENT DOCUMENTS

| | | |
|---|---|---|
| DE | 19509332 | 8/1996 |
| DE | 19507141 | 9/1996 |
| DE | 19720782 | 12/2004 |
| EP | 1121902 | 8/2001 |
| EP | 1190678 | 3/2002 |
| EP | 1474050 | 11/2004 |
| EP | 1570795 | 9/2005 |
| EP | 1579816 | 9/2005 |
| EP | 1634537 | 3/2006 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 2173104 | 10/1986 |
| GB | 2365345 | 2/2002 |
| WO | WO01/49191 | 7/2001 |
| WO | WO02/054966 | 7/2002 |
| WO | WO03/068088 | 8/2003 |
| WO | WO03068083 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/012088 | 2/2006 |
| WO | WO2006/017616 | 2/2006 |
| WO | WO2006/028537 | 3/2006 |

* cited by examiner

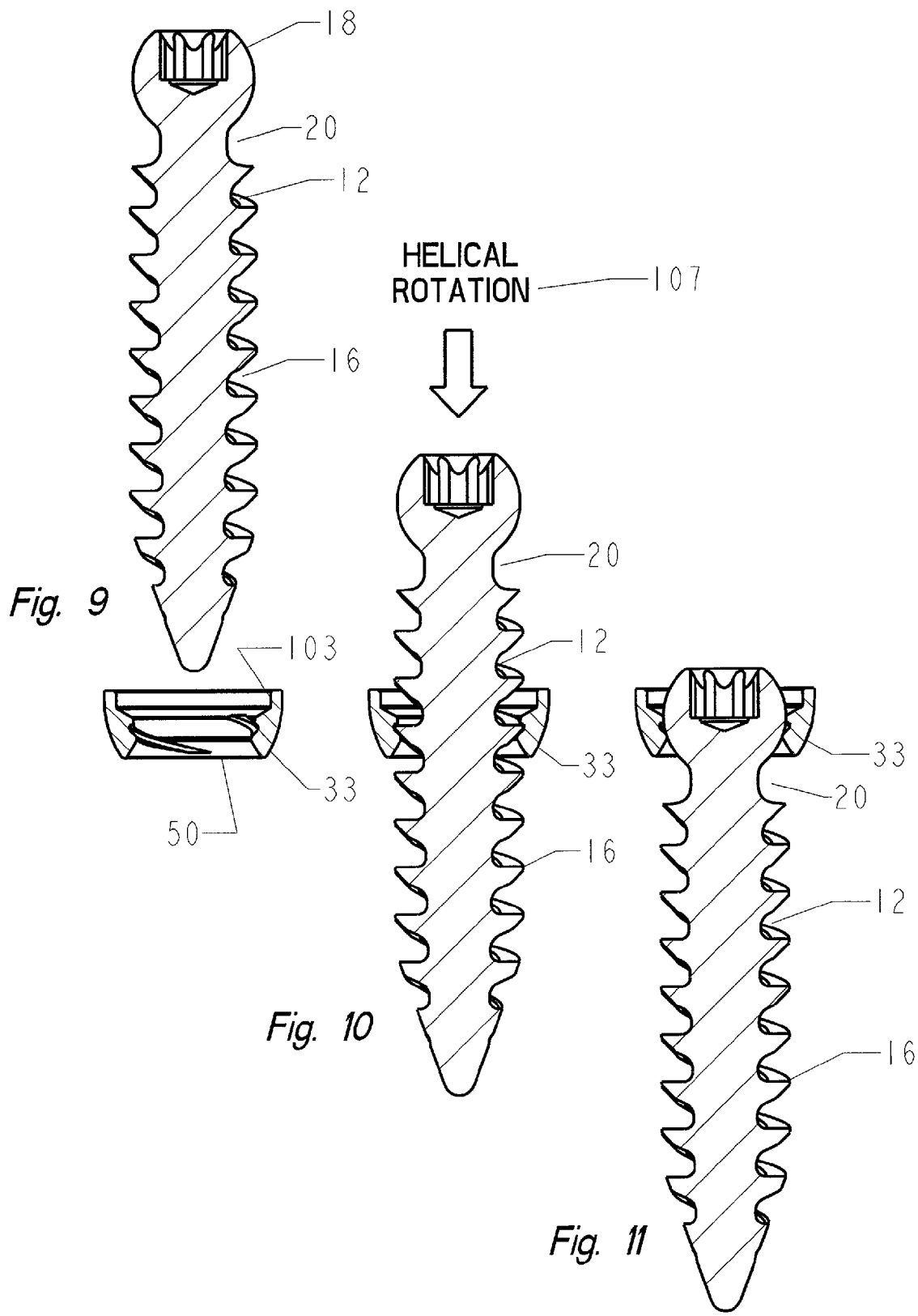

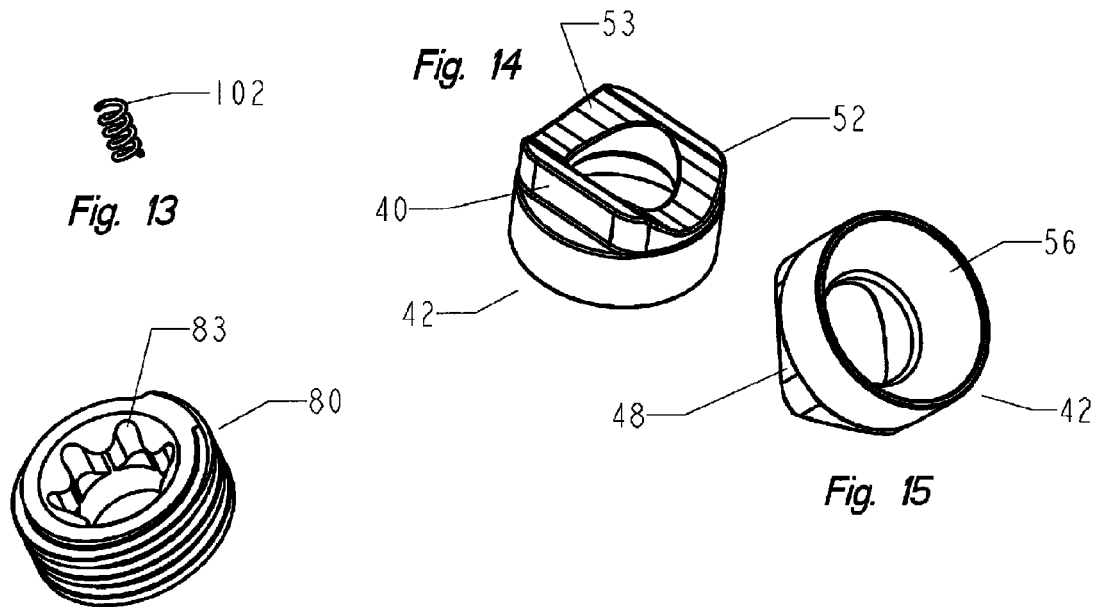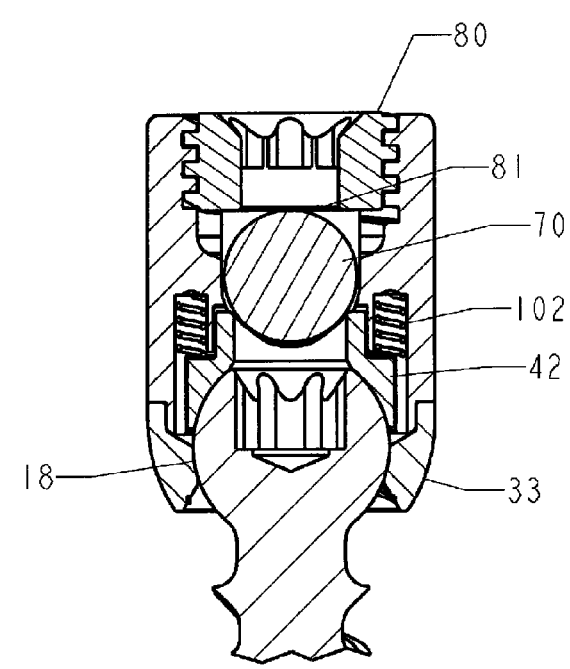

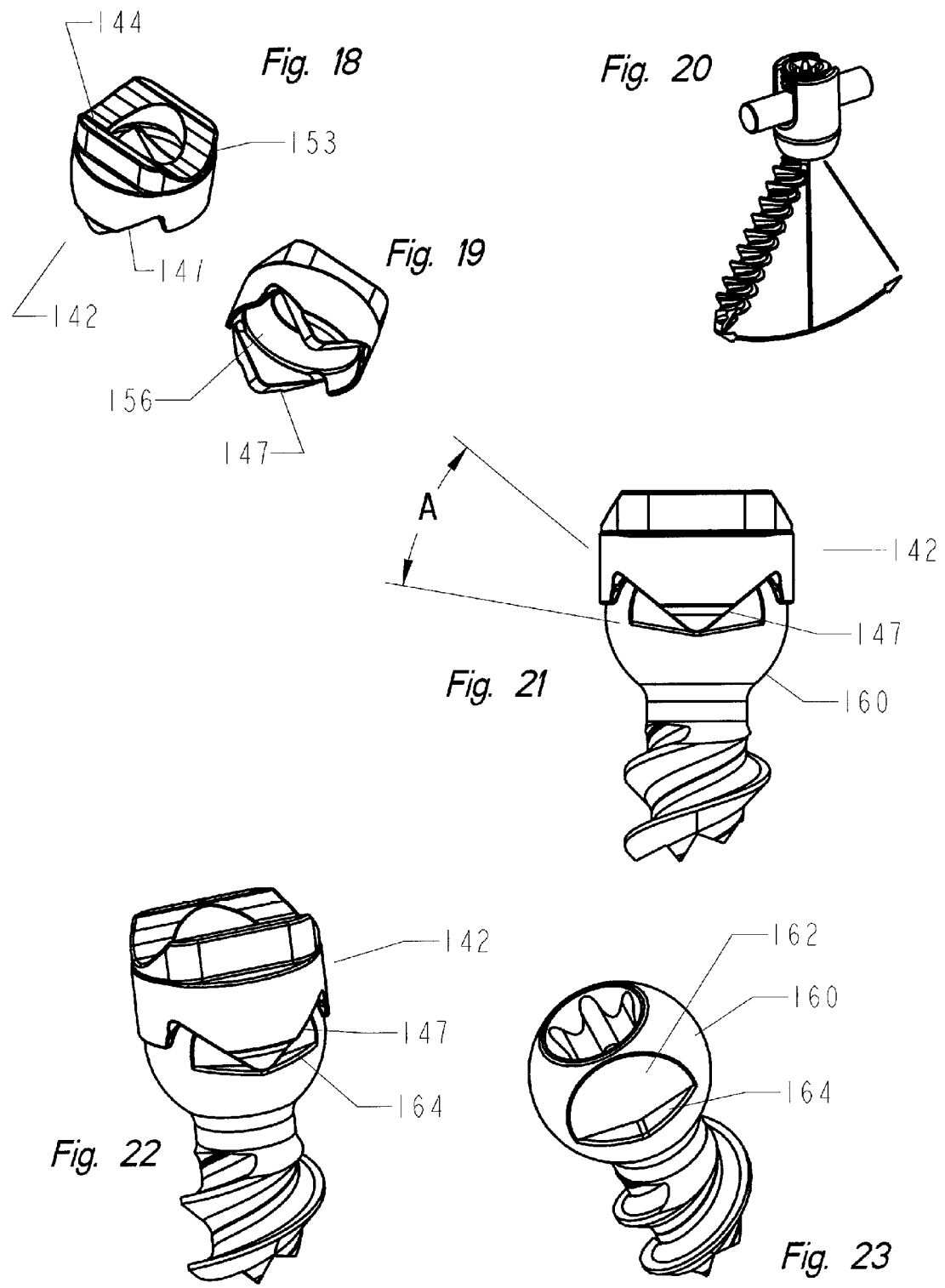

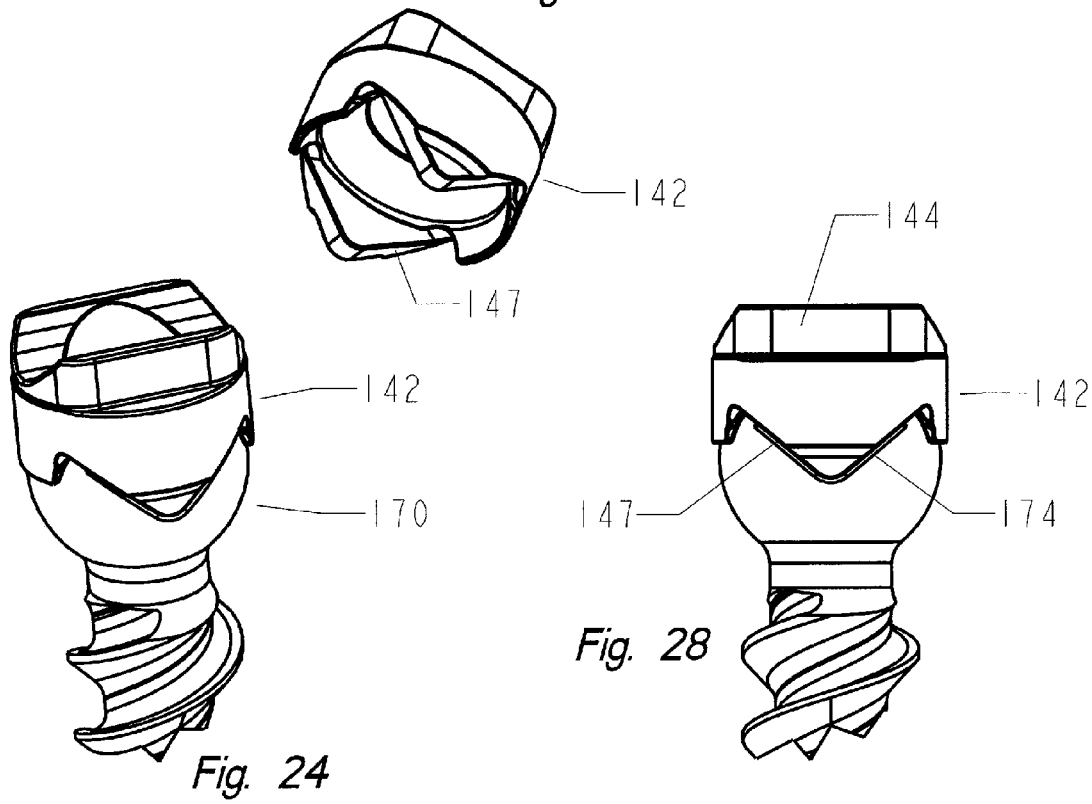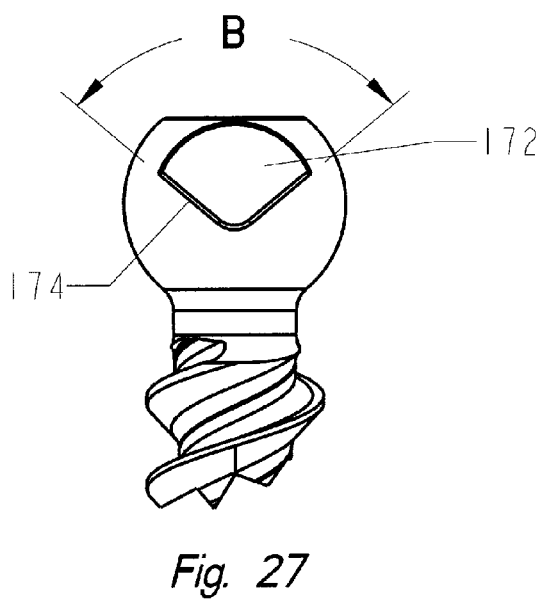

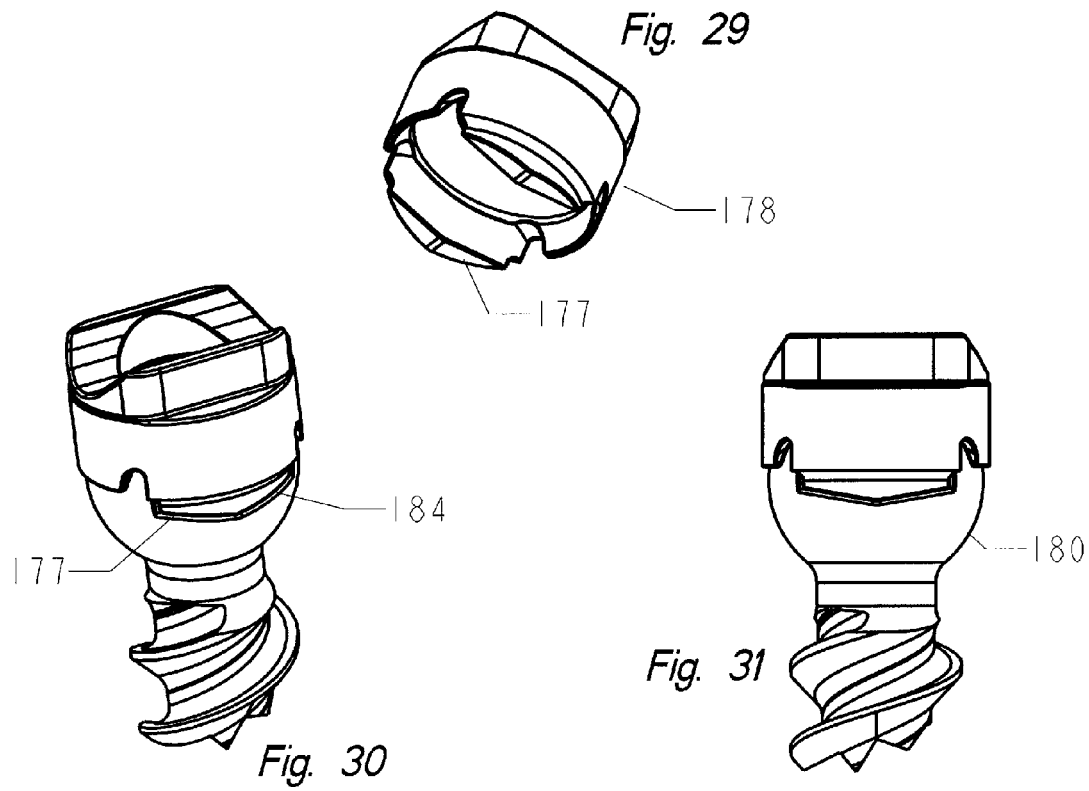
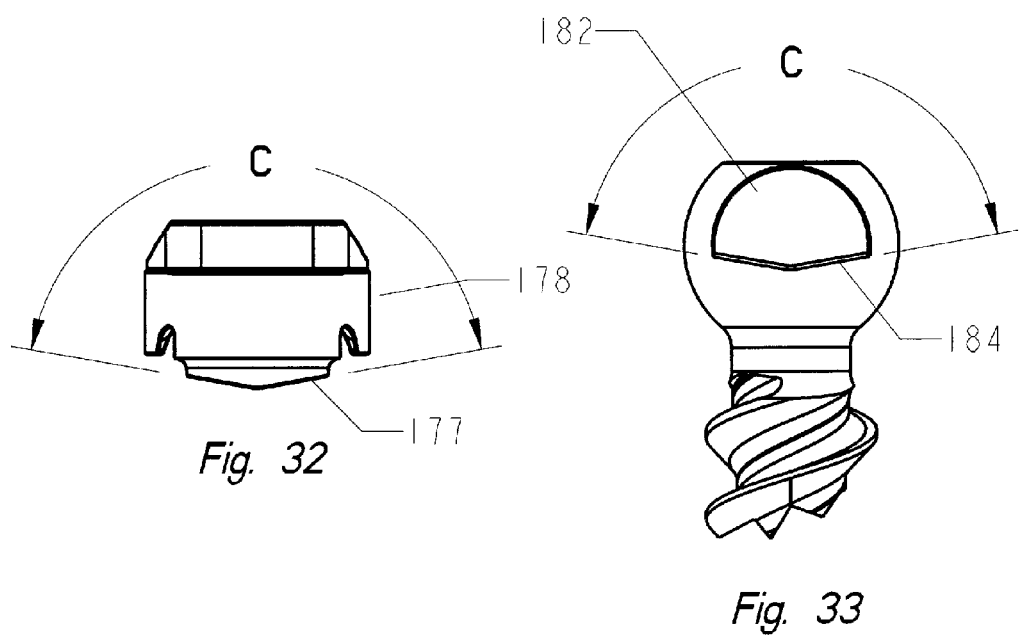

PEDICLE SCREW IMPLANT SYSTEM

PRIORITY CLAIM AND CROSS REFERENCE TO RELATED APPLICATIONS

This application is a continuation-in-part of patent application Ser. No. 12/540,398 filed Aug. 13, 2009 which is a continuation in part of U.S. patent application Ser. No. 11/749,615 filed May 16, 2007 and a continuation in part of U.S. patent application Ser. No. 12/355,145 filed Jan. 16, 2009 the entire contents of these applications are herein incorporated by reference.

FIELD OF THE INVENTION

This invention is directed to the field of pedicle screws, and in particular, to a pedicle screw implant system adapted for use as a polyaxial, mono-axial with range limiting or as a fixed spinal implant with top or side loading for a connector rod.

BACKGROUND OF THE INVENTION

The use of pedicle screw fasteners is well known for their use with spinal fixation systems. In the field of spinal pathologies, spinal fixation systems represent a major medical breakthrough. Surgically implanted fixation systems are commonly used to correct a variety of back structure problems, including those which occur as a result of trauma or improper development during growth. A commonly applied fixation system includes the use of one or more connecting rods aligned in a desired orientation with respect to a patient's spine for stabilization of the spine. The pedicle screw provides anchoring of the fixation system wherein a series of connectors are used to rigidly link rods and the anchors.

Common to all spinal implant systems is the necessity for proper anchoring to the bone so as to provide support for the aforementioned components. The use of a polyaxial design pedicle screw has proven very effective in allowing a surgeon the flexibility to secure an installation with minimal strain on the individual. However, one of the problems with a polyaxial pedicle screw is the lack of a stabilized angular placement position during installation. Once a polyaxial pedicle screw is inserted into the bone, the connector component portion has yet to receive a connecting rod leaving the connector assembly free to move around or fall over making it difficult for the surgeon to grasp while in the midst of surgery. This problem is compounded by the need to align multiple component heads for receipt of a connecting rod. Another problem with the prior art is the inability to use various size anchoring screws in combination with a common saddle larger saddle which leads to assembly integrity over a large range of installation considerations.

A conventional polyaxial bone screw typically consists of a single shaft with a coarse thread at one end for threading into the bone. A spherical ball is positioned at an opposite end for coupling to a connecting member. For example, a number of patents exist for bone screw anchoring assemblies that include a U-shaped connector element which acts as a saddle for attachment to an alignment rod. U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion designed for threadingly engaging a semi-spherical cup for use with a specially designed alignment rod. The alignment rod includes spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting a patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are designed with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900 employs connectors that join the support rods and anchoring screws. The connectors eliminate unwanted relative motion between the rod and the screws, thereby maintaining the patient's spine in a corrected orientation.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths.

U.S. Pat. No. 7,445,627 discloses a fastener and a bone fixation assembly for internal fixation of vertebral bodies. According to one exemplary embodiment, a tulip assembly is employed; the tulip assembly includes a non-circular surface disposed on its outer surface. A fastener is coupled to the tulip assembly and positionable to retain the tulip assembly on the head of a screw. A cap having an outer surface and a plurality of inner protrusions mateably connects to the non-circular surface on the tulip body to compress the tulip assembly to secure a rod.

U.S. Publication No. 2008/0177322 discloses a spinal stabilization system that includes bone fastener assemblies that are coupled to vertebrae. Each bone fastener assembly includes a bone fastener and a collar. The bone fastener has a head portion having at least a first cross-sectional shape in a first plane, and a second cross-sectional shape in a second plane. The collar has a circular opening in the bottom, with a relief extending from the circular opening. The second cross-sectional shape of the bone fastener is keyed to the opening to permit insertion of the bone fastener into the collar assembly from the bottom. After insertion, the bone fastener is rotated to prohibit removal of the bone fastener from the collar. The collar can then be rotated and/or angulated relative to the bone fastener. An elongated member can be positioned in the collar and a closure member is then used to secure the elongated member to the collar.

U.S. Publication No. 2006/0241599 discloses a polyaxial fixation device having a shank with a spherical head formed on a proximal end thereof, and a receiver member having an axial passage formed therein that is adapted to polyaxially seat the spherical head of the shank. The polyaxial bone screw further includes an engagement member that is adapted to provide sufficient friction between the spherical head and the receiver member to enable the shank to be maintained in a desired angular orientation before locking the spherical head within the receiver member.

U.S. Publication No. 2006/0235392 discloses a system for connecting a fastener element (e.g., a pedicle screw) relative to a rod for the purposes of vertebral fixation. The system may permit multi-axial movement between the fastener element and the rod. Further, the system may permit the angular relationship between the fastener element and the rod to be held in a desired orientation.

U.S. Publication No. 2006/0155277 discloses an anchoring element for securing a rod on a vertebra, that comprises a retaining means for receiving the rod, a safety element placed on the retaining means, a securing element which can be placed on the body of the vertebra, and a clamping device which is arranged between the retaining means and the securing element. The clamping device includes a ring-shaped mount, a partially conical-segment shaped bearing and an intermediate element which is embedded in the mount and which engages the bearing, whereby the mounting is moveable in a removed state in relation to the bearing, whereas the mount is maintained in a clamped state on the bearing by means of the intermediate element. The mount is rigidly connected to the retaining means and the bearing is rigidly connected to the securing element.

U.S. Publication No. 2006/0149240 discloses a polyaxial bone screw assembly that includes a threaded shank body having an upper capture structure, a head and a multi-piece retainer, articulation structure. The geometry of the retainer structure pieces correspond and cooperate with the external geometry of the capture structure to frictionally envelope the retainer structure between the capture structure and an internal surface defining a cavity of the head. The head has a U-shaped cradle defining a channel for receiving a spinal fixation or stabilization longitudinal connecting member. The head channel communicates with the cavity and further with a restrictive opening that receives retainer pieces and the capture structure into the head but prevents passage of frictionally engaged retainer and capture structures out of the head. The retainer structure includes a substantially spherical surface that mates with the internal surface of the head, providing a ball joint, enabling the head to be disposed at an angle relative to the shank body.

U.S. Pat. No. 6,716,214 discloses a polyaxial bone screw having a bone implantable shank, a head and a retaining ring. The retaining ring includes an outer partial hemispherical surface and an inner bore with radially extending channels and partial capture recesses. The shank includes a bone implantable body with an external helical wound thread and an upwardly extending capture structure. The capture structure includes at least one spline which extends radially outward and has a wedged surface that faces radially outward therefrom. The capture structure operably passes through a central bore of the retaining ring while the spline passes through a suitably shaped channel so that the spline becomes positioned above the head, at which time the shank is rotated appropriately and the shank is drawn back downwardly so that the spline engages and seats in the capture recess. The head includes an internal cavity having a spherical shaped surface that mates with the ring surface and has a lower restrictive neck that prevents passage of the ring once the ring is seated in the cavity.

U.S. Pat. No. 6,565,567 discloses a pedicle screw assembly for use with a rod for the immobilization of bone segments. The assembly is comprised of a screw, a polyaxial housing for receiving the screw, a washer, a set screw, and a cup-shaped cap. The lower portion of the housing terminates in a reduced cross-sectional area, which engages the bottom of the screw head. When the screw is placed inside the polyaxial housing and the screw is secured into the bone, the polyaxial housing is pivotable with three degrees of freedom. The housing includes a top portion with a pair of upstanding internally threaded posts. A washer is inserted between the head of the screw and the rod. A cap, having a bottom, with a pair of posts accommodating openings and a lateral cross connector, is placed over the posts so that the cross connector engages the rod. The cross connector and washer have concave generally semi-cylindrical rod engaging surfaces to prevent the rod from rotating or sliding within the housing once the set screw is tightened. A set screw is threaded into the housing posts to secure the rod within the housing. The washer has a roughened lower surface which, in conjunction with the reduced cross-sectional area at the bottom of the housing, securely clamps and locks the housing to the screw head when the set screw is tightened.

U.S. Pat. No. 5,501,684 discloses an osteosynthetic fixation device which consists of a fixation element which has a conical head section and an anchoring element abutting it which is for attachment into the bone. The fixation device also consists of a spherically formed, layered, slotted clamping piece which has a conical borehole for installation of the conical head section, and which is meant for locking within a connecting piece equipped with a spherically shaped layered borehole. Fixation piece has an axially arrayed tension element, permitting axial displacement and wedging of conical head section in the borehole that corresponds with it. The fixation device is appropriate for use as a plate/screw system, an internal or external fixator, and in particular for spinal column fixation.

U.S. Pat. No. 4,693,240 discloses a bone pin clamp for external fracture fixation. The apparatus comprises rotation, slide and housing elements nested one within the next, each such element having an aperture to receive a pin therethrough, and the rotation and slide elements respectively affording pin adjustment in azimuth and zenith, and in height, relative to the housing element. A locking mechanism including a common actuator member is operable simultaneously to lock the pin and rotation and slide elements in the housing element. In a preferred form, the housing element serves as a cylinder with the slide element as a keyed piston therein, and the rotation element is a disc located between a screw and annular thrust members engaged in the piston, the piston and disc being split respectively to lock by expansion and compaction under screw action towards the thrust members.

U.S. Pat. No. 4,483,334 discloses an external fixation device for holding bone segments in known relation to each other. The device includes a pair of bone clamp assemblies each secured to bone pins extending from the bone segments, a bridge extending between the pin clamp assemblies, and a specialized high friction universal assembly connecting the bridge to each of the pin clamp assemblies.

U.S. Pat. No. 4,273,116 discloses an external fixation device for reducing fractures and realigning bones that includes sliding universal articulated couplings for enabling easy adjustment and subsequent locking of connections between Steinmann pins and tubular tie-rods. The couplings each include a split, spherical adapter sleeve which is embraced by the matching inner surface of an open ring portion of a coupling locking clamp having clamp lugs tightenable against a block by means of a nut-and-bolt assembly. Further nut-and-bolt assemblies are disposed in elongated slots in the blocks and cooperate with associated clamping members to clamp the Steinmann pins to the blocks after adjustment in two orthogonal directions and optional resilient bending of the pins.

U.S. Pat. No. 6,672,788 discloses a ball and socket joint incorporating a detent mechanism that provides positive biasing toward a desired position. The ball and socket joint can be used in flexible supports that hold and support items such as lamps, tools and faucets. The detent mechanism comprises two corresponding parts, one in the ball portion and the second in the socket portion of the joint. The first detent part is a protrusion of some type and the second detent part is a groove or indentation that is adapted to accept and engage the protrusion. If the ball contains the detent protrusion, then the socket contains the detent indentation. And conversely, if the socket contains the detent protrusion, then the ball contains the detent indentation. The detent tensioning force can be provided by a spring or a spring band, the characteristics of the material from which the joint is made, or by some other similar tensioning device.

U.S. Publication No. 2003/0118395 discloses a ball and socket joint, which has a housing, a ball pivot mounted pivotably in the housing, and a sealing bellows, which is fastened to the housing and is mounted on the ball pivot slidably via a sealing ring provided with two legs. A first leg of the two legs is in contact with the ball pivot under tension and the second leg meshes with the wall of the sealing bellows. The second leg is, furthermore, fastened in an anchoring ring arranged at least partially in the wall of the sealing bellows.

U.S. Pat. No. 4,708,510 discloses a ball joint coupling assembly that permits universal movement and positioning of an object with respect to a vertical support shaft. Quick release/lock action is provided by a ball joint assembly having a housing in which a ball and piston are movably coupled. The ball is captured between annular jaw portions of the housing and piston, with locking action being provided by gripping engagement of the piston jaw portion and the housing jaw portion. The ball member is gripped in line-contact, compressive engagement by the annular edges of the piston jaw and housing jaw on opposite sides of the ball. The piston is constrained for axial movement within the housing with locking engagement and release being effected by rotation of a threaded actuator shaft.

U.S. Pat. No. 3,433,510 discloses a swivel structure for rigidly joining first and second parts together. A first member is connected to the first part and a second member is connected to the second part. An intermediate hollow member interconnects the first and second members together. An enlarged outer end portion is provided on the first member and includes a plurality of locking means thereon. Means are provided on the second member for engaging one of the locking means. Means are provided for threadably joining the hollow member and the second member together. A slot is provided in the hollow member and includes an enlarged entrance which passes the enlarged outer end portion and which also includes a restricted opening opposite the threaded joining of the hollow member and the second member together. The portion surrounding the restricted opening opposes the forces imparted against the outer end portion as the second member is threadably joined to the hollow portion and bears against the outer end portion.

U.S. Patent Publication No. 2008/0269809 discloses a bottom loading pedicle screw assembly. The device includes a pedicle screw and a connector member. The pedicle screw includes a threaded lower portion while the upper portion includes a groove sized to accept a clip member. The clip member includes a spherical outer surface. In operation the clip is placed within the groove and the assembly is pressed through the opening in the bottom of the connector member. While the device is bottom loading, the device will separate when the pedicle screw is aligned with the connector member. The construction of the clip member allows the clip to collapse sufficiently to pass back through the opening when the screw is positioned in alignment with the connector, requiring the connection to bone be placed at an angle with respect to the connector for proper operation.

Various attempts have also been made for placing of a connecting rod along a side entry chamber. U.S. Pat. Nos. 5,669,911; 5,817,094 and 5,690,630 discloses a polyaxial pedicle screw having a side loading channel with an external nut fastened to the connector for securing a rod to the screw.

U.S. Pat. No. 6,063,090 discloses a device for connecting a longitudinal support to a pedicle screw. One embodiment including a sidewardly open channel for receipt of a longitudinal support; the device employs a clamping element having a hollow truncated cone shape with a plurality of slots, the element used in securing the fastener in the tapered opening.

U.S. Pat. No. 7,022,122 discloses a device for connecting a longitudinal bar to a pedicle screw. The device including an adjusting nut for securing the spherical head of a pedicle screw with the longitudinal bar.

Thus, what is needed is a pedicle screw system that can be adapted for use in a spinal fixation system that includes a thread thru assembly allowing different sized anchoring screws to be coupled to a single size connector, and an assembly that maintains the connector member in position to assist a surgeon during installation. The pedicle screw system to include a polyaxial and monoaxial configuration, as well as fixed angular positioning therebetween. In addition, the pedicle screw system to include side loading and top loading.

SUMMARY OF THE INVENTION

The present invention is a pedicle screw system that allows for securement to a bone screw in either a polyaxial, monoaxial, fixed or range limiting attachment. In the preferred embodiment the threads of a pedicle screw can pass thru a lower section of a connecting member during manufacturing which permits the manufacturer to use a range of different size shanks and threads while using a common connector member to lower inventory costs. The system also provides for using oversized pedicle screws for a given connector member to provide a low profile assembly. In addition, the system includes a means for applying tension to the pedicle screw anchoring member that allows the connector to be desirably positioned relative to the screw to assist in surgical assembly of the system.

The bone screw has a threaded shank extending outwardly from a spherical ball for use in anchoring to the spine and a connector member that includes a socket constructed and arranged to accept the spherical ball. In the disclosed embodiment, the connector member is illustrated as a U-shaped or side loading connector member having a lower receptacle that operates as a socket for housing a retainer ring. The socket is receptive to the spherical ball which is inserted through the top of the connector during a manufacturing step. The retainer ring is biased against an upper component of the connector member and engages the spherical ball so as to keep the connector member in position during installation and prior to installation of the connector rod. A surgeon can easily move the connector member into a preferred position and the biasing member keeps sufficient tension on the retainer ring so as to maintain the connector in a position for proper placement of the connecting rod. This facilitates easier installation of the connecting rod by maintaining the proper angle of the saddle also allowing the surgeon to align additional screws on adjacent vertebra and/or bone structures.

The retaining ring may have a concave spherical shape that cooperates with a spherical head portion on the bone screw allowing the bone screw to operate in a polyaxial manner. Alternatively the retaining ring may include a partial spherical cavity shaped to cooperate with a partially spherical head portion to cause the bone screw to operate in a monoaxial range of motion or further include angular construction so as to limit the range of motion to a reduced or fixed angular displacement. Alternatively, the head portion of the bone screw may be shaped to cause range limitation in accordance with the shape of the retaining ring.

A fastener member, such as a set screw or nut, is utilized to press the retaining ring into contact with the spherical or partially spherical head while simultaneously causing the lower split ring to engage a lower portion of the ball as it wedges between the ball and the inner surface of the connector member immobilizing the connection.

The connector members are substantially rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the present invention to teach the use of a pedicle screw system for posterior fixation having a common connector for use with different sized threaded shanks and thread types, which lowers inventory requirements and provides the surgeon with a uniform connector.

It is another objective of the present invention to disclose the use of a pedicle screw having a biasing member to supply a tension between the anchoring member and the connector member, the tension facilitates installation by maintaining the connector component in an angular placement position as desired by the surgeon prior to assembly of the rod member.

It is another objective of the present invention to teach the use of a bone screw assembly having a connector assembly that provides a thread through lower portion and a heavy side-walled upper portion that does not include thread through to provide a greater safety factor when a set screw fastener is employed to avoiding splaying.

Another objective of the present invention to teach the use of a polyaxial bone screw assembly that is adapted to utilize multiple connector rod member diameters.

Still another objective of the present invention to teach the use of a retainer ring member for use in conjunction with a U-shaped saddle or side loading saddle to obtain a three point fixation between a fastener set screw and the saddle.

Yet another objective of the present invention to teach the use of a polyaxial bone screw assembly that allows 60 degrees of conical polyaxial motion.

It is yet another objective of the present invention to provide a simple spinal fixation system having only a few components for use in assembly and limiting component parts needed during assembly by use of a common connector.

Still another objective of the invention is to teach a motion limiting pedicle screw assembly.

Still yet another objective of the present invention is to teach a pedicle screw assembly that utilizes a cooperating retaining ring and bone screw head to provide a pedicle screw that can be fixed, monoaxial or polyaxial in movement.

Still yet another objective of the present invention is to teach a pedicle screw assembly that that utilizes a cooperating retaining ring and bone screw head to provide a pedicle screw having a fixed or predetermined angular displacement.

Still another object of the invention to teach the use of a bone screw assembly having a connector assembly that provides a pass through non threaded lower portion with at least one groove on the spherical seat surface to provide improved friction gripping between the spherical seat surface and the spherical head of the pedicle screw.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 9 is a cross sectional side view in an exploded manner depicting a bone screw with a thread thru lower element of a connector;

FIG. 10 is a cross sectional side view of a bone screw partially threaded into a lower element of a connector;

FIG. 11 is a cross section side view of a bone screw threaded into a lower element of a connector;

FIG. 13 is a perspective view of the biasing spring;

FIG. 14 is a top perspective view of the retainer ring element;

FIG. 15 is a bottom perspective view of the retainer ring element;

FIG. 16 is a perspective view of the set screw;

FIG. 17 is a cross section view of the assembled connector for a polyaxial assembly;

FIG. 18 is a top perspective view of the limiting retainer ring element;

FIG. 19 is a bottom perspective view of the limiting retainer ring element;

FIG. 20 is a pictorial view depicting monoaxial range of motion;

FIG. 21 is a side view of a monoaxial bone screw and retaining ring;

FIG. 22 is a perspective view of a monoaxial bone screw and retaining ring;

FIG. 23 is a perspective view of a monoaxial bone screw;

FIG. 24 is a perspective view of a monoaxial bone screw and retaining ring of an alternative embodiment;

FIG. 25 is a bottom perspective view of a limiting retainer ring element;

FIG. 26 is a side view of a limiting retainer ring element;

FIG. 27 is a perspective view of a monoaxial bone screw;

FIG. 28 is a perspective view of a monoaxial bone screw and retaining ring of an alternative embodiment;

FIG. 29 is a bottom perspective view of a limiting retainer ring element;

FIG. 30 is a perspective view of a monoaxial bone screw and retaining ring of an alternative embodiment;

FIG. 31 is a side view of a monoaxial bone screw and retaining ring of an alternative embodiment;

FIG. 32 is a side view of a limiting retainer ring element;

FIG. 33 is a perspective view of a monoaxial bone screw;

DETAILED DESCRIPTION OF THE PREFERRED EMBODIMENT

Figure 1:
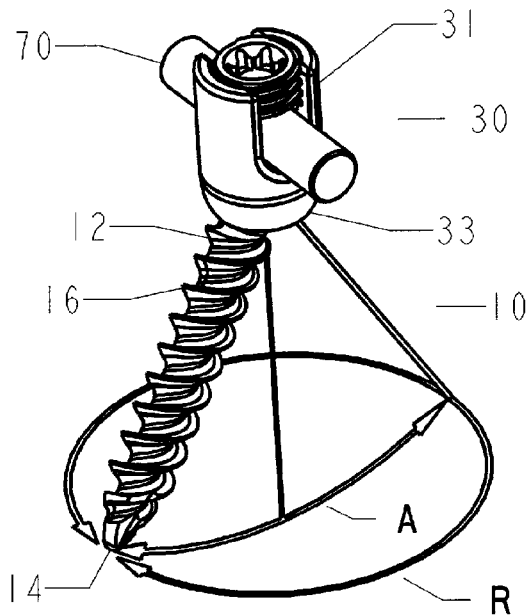
FIG. 1 is depiction of the instant invention having a U-shaped connector with a polyaxial assembly.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to the Figures, disclosed is an exemplary embodiment of the thread thru polyaxial pedicle screw system for use in a spinal fixation system. The pedicle screw system (10) is based on an anchoring member formed from a bone screw (12) including a shank (14) with at least one helical thread (16) formed along the length thereof. It is important to note that the proportions of the bone screw depicted are for illustrative purposes only and variations in the length of the shank, diameter of the screw, thread pitch, thread length, number of thread leads, shank induced compression and the like may be varied without departing from the scope of the invention. As will be further described later in this specification, unique to invention is the ability to use various shank widths and thread sizes with the same connector which reduces the manufacturing inventory. At the upper end (20) of the shank (14) is a ball shaped spherical connector (18) having a predetermined diameter. The diameter of the spherical connector (18) and the width of the shank (20) control the angular positioning (A) of about 60 degrees that the shank has of conical polyaxial motion in relation to the connector assembly (30).

FIG. 1 depicts a connector assembly (30) that is U-shaped and includes an upper connector member (31) and a lower connector member (33) having a polyaxial bone screw with movement depicted throughout a radius (R) which is controlled by a retainer ring construction (42), described in detail later in this specification, or by construction of the ball shaped connector (18). The angular positioning of the bone screw having a predetermined angular displacement (A).

Figure 2:
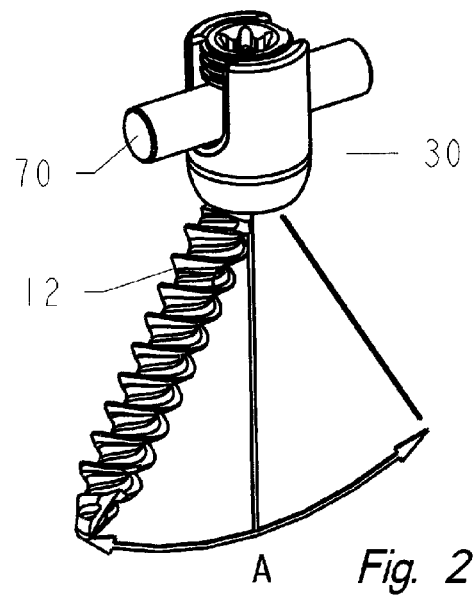
FIG. 2 is depiction of the instant invention having a U-shaped connector with a monoaxial assembly.
Figure 3:
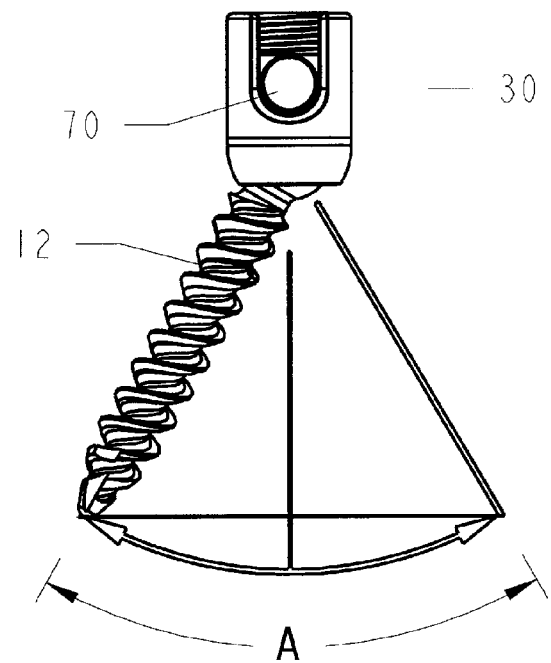
FIG. 3 is side view depiction of the range of motion for instant invention having a U-shaped connector with either a polyaxial or monoaxial assembly.

FIG. 2 depicts a monoaxial bone screw having a mono angular predetermined angular displacement (A). FIG. 3 depicts a side view of either FIG. 1 or FIG. 2 wherein the predetermined angular displacement (A) is controlled by a retainer ring construction (42) or by construction of the ball shaped connector (18), described in detail later in this specification.

Figure 4:
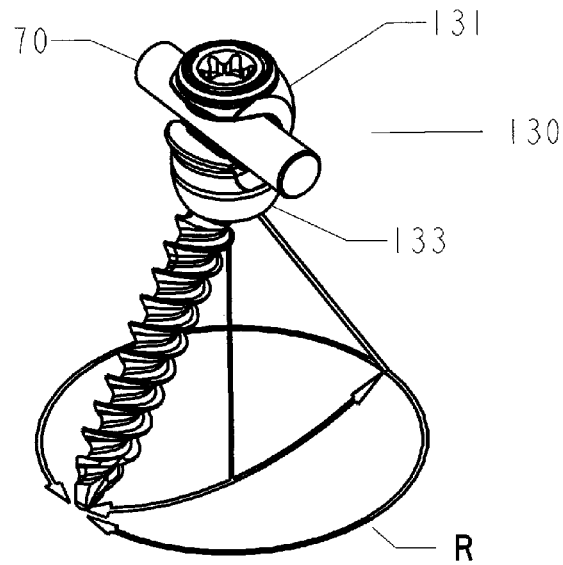
FIG. 4 is depiction of the instant invention having a side loading connector with a polyaxial assembly.

FIG. 4 depicts a connector assembly (130) that allows for side loading and includes an upper connector member (131) and a lower connector member (133) having a polyaxial bone screw with movement depicted throughout a radius (R) which is controlled by a retainer ring construction (42), described in detail later in this specification, or by construction of the ball shaped connector (18). The angular positioning of the bone screw having a predetermined angular displacement (A). The connector (131) is in receipt of a connecting rod 70.

Figure 5:
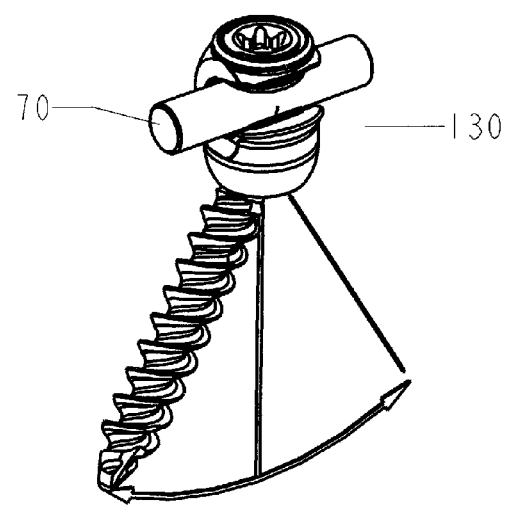
FIG. 5 is depiction of the instant invention having a side loading connector with a monoaxial assembly.
Figure 6:
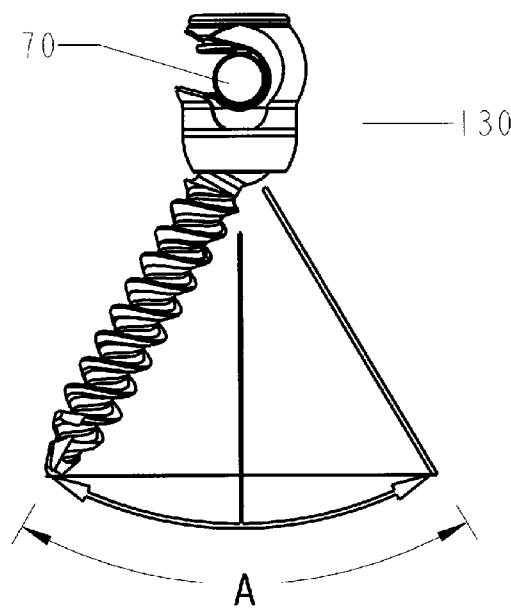
FIG. 6 is side view depiction of the range of motion for instant invention having a side loading connector with either a polyaxial or monoaxial assembly.

FIG. 5 depicts a monoaxial bone screw having a mono angular predetermined angular displacement (A). FIG. 6 depicts a side view of either FIG. 4 or FIG. 5 wherein the predetermined angular displacement (A) is controlled by a retainer ring construction (42) or by construction of the ball shaped connector (18), described in detail later in this specification.

Figures 7, 8:
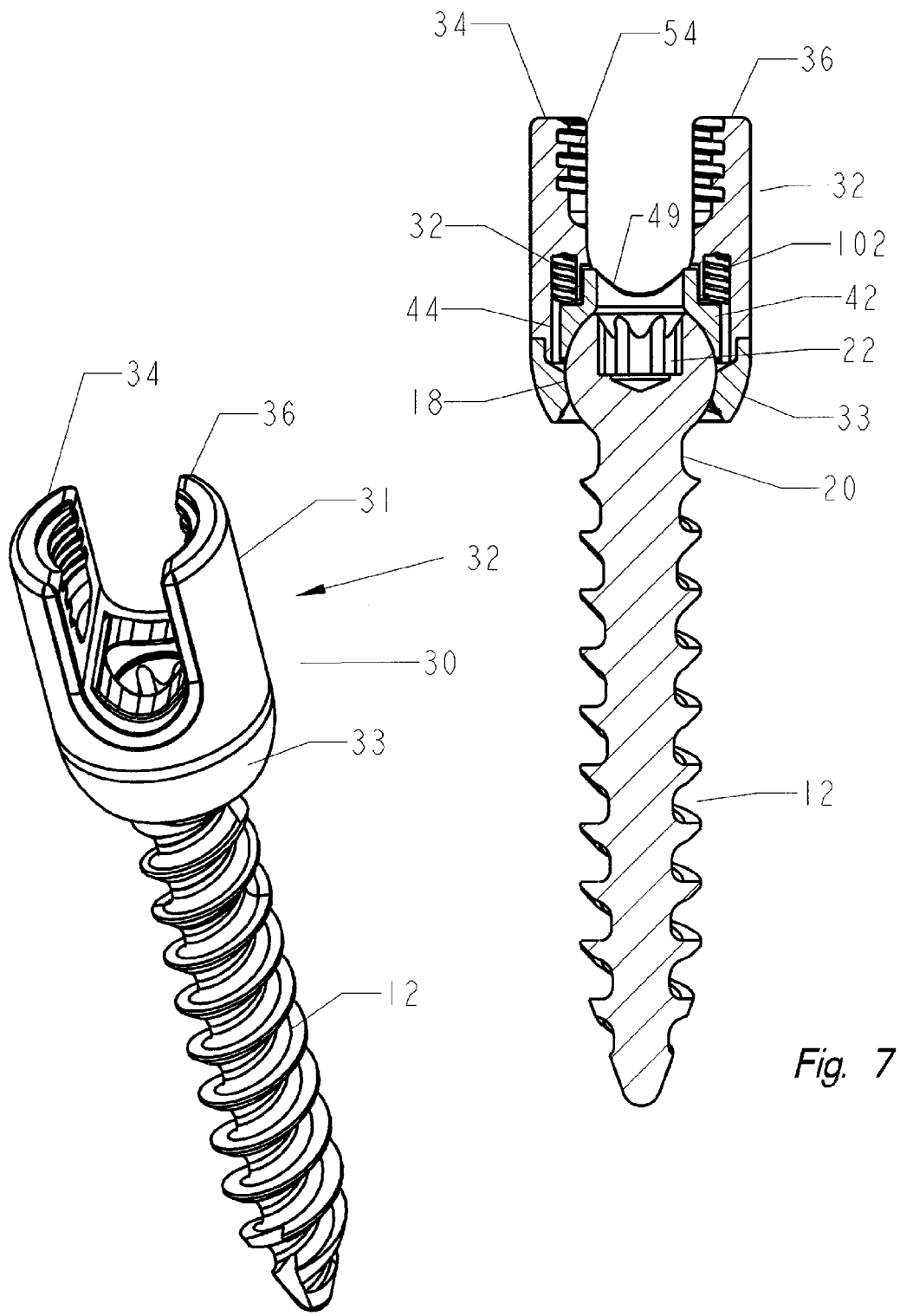
FIG. 7 is a perspective view of the pedicle screw apparatus without a rod or set screw.
FIG. 8 is a cross section view of the thread thru pedicle screw apparatus.
Figure 12:
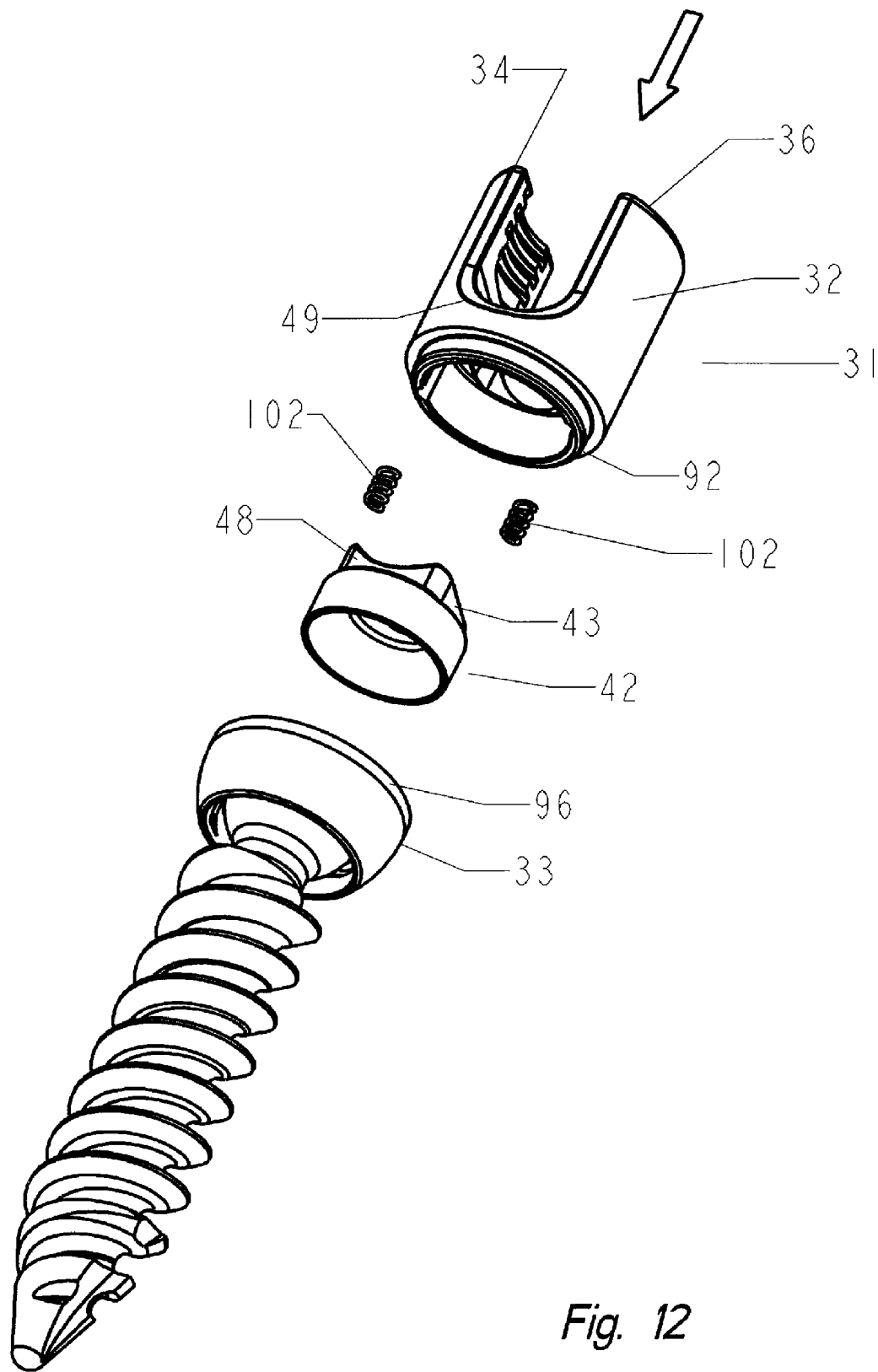
FIG. 12 is an exploded cross section view of the U-shaped pedicle screw apparatus.
Figure 34:
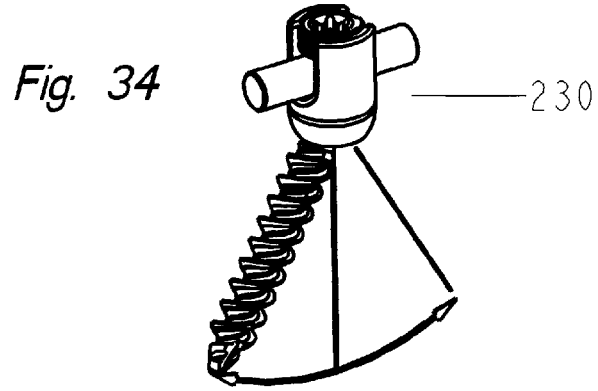
FIG. 34 is a pictorial view depicting monoaxial range of motion.

As shown in FIGS. 7, 8 and 12, the U-shaped connector 30 has an upper connector member (31) with a substantially circular side wall (32) divided by a pair of U-shaped openings (49) forming an upstanding first interior side wall (34) and second interior side wall (36). A portion of each said side wall is threaded (54) for receipt of a set screw used in securing a rod within the connector. The connector assembly is sized to cooperate with the retaining ring (42) for receipt of various sized rods, as well as limiting the range of motion of between the connector (30) and the screw (12). A driver receptacle (22) is located along the upper end (20) of the spherical connector for use in installing the bone screw. It should be noted that the driving receptacle may be any shape, male or female, suitable for cooperation with a driving tool to rotate the bone screw into its final position.

The upper connector member (31) preferably includes a shoulder (92) on the bottom surface thereof for location of the lower connector member (33) forming a socket area (44) for receipt of a retainer ring (42) there between. The socket area (44) is constructed and arranged to cooperate with the spherical ball connector on the bone screw and is further designed to prevent rotation of the retainer ring (42) thereby maintaining the saddle surface area in alignment with the U-shaped opening. Alignment is maintained by inset side walls (45, 46) which operate in conjunction with side walls (43, 48) of the retainer ring (42).

The lower connector member (33) also includes a shoulder (96) that is constructed and arranged to cooperate with shoulder (92) to maintain alignment of the two components. The lower connector member (33) includes a substantially spherical shaped receptacle (38) which operates in conjunction with the upper component member to house the retainer ring (42) used to engage the spherical ball (18). The shoulders (92) and (96) are utilized to align the components and the upper and lower connector members, once assembled the connector members are laser welded together. It should be noted that other suitable methods or techniques of attaching the upper and lower connector members together may be utilized without departing from the scope of the invention, such methods may include, but should not be limited to spot welding, threads, adhesives, pins swaging, solder, interference fits and suitable combinations thereof.

The retainer ring (42) is positioned within the lower receptacle (38) with an upper edge (52) positionable within the cavity formed by side wall (41); the retaining ring side wall (43) cooperates with side wall (41) of the cavity to prevent rotation of the retaining ring. The inner surface (56) of the retaining ring has a spherical diameter and provides for self centering by engaging of the outer surface of the spherical connector (18). The upper surface (53) of the retaining ring (42) includes a concave cylindrical surface for cooperation with the connecting rod (70). The cylindrical surface provides additional surface area for contact with the connecting rod and may include a knurled or otherwise modified surface finish adapted to enhance gripping power between the rod and the connecting assembly (30). The retaining ring (42) includes a biasing member to cause a tension from the retaining ring (42) to the spherical ball (18). In the preferred embodiment the biasing member is coil springs (102) that are located to cooperate with spring pockets (100) positioned in the upper connector member to locate and contain coil springs (102). The spring members bias the retaining ring toward the opening (50) of the lower receptacle. It should be noted that while springs are depicted, the biasing member can be a polymer or any other resilient material that can be use to apply a light pressure onto the retaining device to maintain a separation. Once the anchoring member is secured to the bone, a rod placed within the connector assembly fits within the U-shaped saddle (49) and is placed on the surface (53) of the retainer ring. The set screw (80) is threaded onto the threads (54) of the upper connector (31) wherein the rod forces the retainer ring (42) onto the spherical ball connector (18) locking the assembly into a fixed position. Alternatively the upper connector member can include the use of the well know faster type wherein the upper connector member had an external thread and the fastener element would be a nut having internal threads.

The surface (53) of the retainer ring (42) includes a clamp angle that provides positive contact with the rod connection member along multiple points with the exact point position dependant upon the diameter of the connecting rod. A third point is supplied by the bottom of the set screw (80) creating three point securement when used with any diameter rod. A driver receptacle (83) is located along the upper end of the set screw (80) for use in installing, the driving receptacle may be any shape, male or female, suitable for cooperation with a driving tool to rotate the set screw into its final position.

The pedicle screw system (10) is a pass through along a portion of the device allowing a larger bone screw to be used without increasing the size of the connector. FIGS. 9-11 depict the steps of selecting an anchoring member having a threaded shank (16) of an elected size for a particular installation. The shank may be small or large, the threads may be small or large, or any combination therebetween. The threaded shank) is inserted into the opening (50) of the lower connector member (33), the lower connector member having a centrally disposed aperture which is constructed and arranged to allow the threaded shank to pass through. The lower connector member (33) includes a pass through thread (103) which allows the larger threaded shanks to pass through by matching the threaded shank with the pass through thread. In operation, an oversized bone screw can be installed by use of a helical rotation (107) wherein the bone screw is threaded through the member (33). The pass through thread (103) having a helical assembly groove to match the bone screw threads. The connector remains the same size and is situated in the socket (96), the design allowing a variety of anchor screws to be inventoried yet only one size connector assembly needs to be inventoried. It should be noted that the spherical head (20) of the bone screw engages the thread of the lower connector in a uniform manner wherein the edge of the thread provide a superior edge for gripping of the head.

Once the anchoring screw is positioned, the retainer ring is placed in the socket (96), the retainer ring (42) having a lower spherical surface (56) positionable along an upper surface of the spherical connector (18), the upper surface (53) of the retainer ring constructed and arranged to receive a connecting rod. A clearance aperture (61) allows passage of a driver for use in securing to the bone screw fastener (22). The spring member (102) is attached to the upper connector (31) having the spring pockets (100). The upper connector member is then coupled, or welded as previously mentioned, to the lower connector member engaging the springs to bias the retainer ring against the anchoring member.

Now referring to FIGS. 18-35 set forth is an embodiment of the limiting retainer ring element (142) for limiting the movement of an anchoring screw in a monoaxial direction. A first embodiment employs a shaped cavity within the retainer ring; a second embodiment employs a shaped spherical head on an anchoring screw. It will be obvious to one skilled in the art that either embodiment accomplishes the inventor's goals, as would a combination of the embodiments. The retainer ring (142) includes an upper wall (144) for use in cooperating with the side wall of a connector cavity to prevent rotation of the retaining ring. The inner surface (156) of the retaining ring has a spherical diameter and provides for self centering by engaging of the outer surface of the spherical connector (160). The upper surface (153) of the retaining ring (142) includes a concave cylindrical surface for cooperation with a connecting rod. The cylindrical surface provides additional surface area for contact with the connecting rod and may include a knurled or otherwise modified surface finish adapted to enhance gripping power between the rod and the connecting assembly. A lower portion (147) of the retaining ring (142) includes a shape adapted for placement over a shaped spherical connector (160) which in a first embodiment includes a recessed area (162) having a substantially flat abutment surface (164). The lower portion (147) of the retaining ring limiting range of monoaxial movement in accordance with the angle of the lower portion (147) in respect to the flat abutment surface (164).

In an alternative embodiment the lower portion (147) of the retaining ring (142) includes a shape adapted for placement over a shaped spherical connector (170) which in this embodiment includes a recessed area (172) having a substantially flat abutment surface (174). The lower portion (147) of the retaining ring limiting range of movement to and angle set by B which in this embodiment is zero, however, changing of angle B on the retainer ring or the spherical head would allow for monoaxial range of motion.

As previously mentioned, the spherical head of the bone screw may include a variation of the above embodiments. FIGS. 29-23 depict the lower portion (177) of the retaining ring (178) to include a shape adapted for placement over a shaped spherical connector (180) which in this embodiment includes a recessed area (172) having an angled abutment surface (184). The lower portion (177) of the retaining ring limiting range of movement to and angle set by C which in this embodiment is zero, however, changing of angle C on the retainer ring or the spherical head would allow for monoaxial range of motion.

Figure 35:
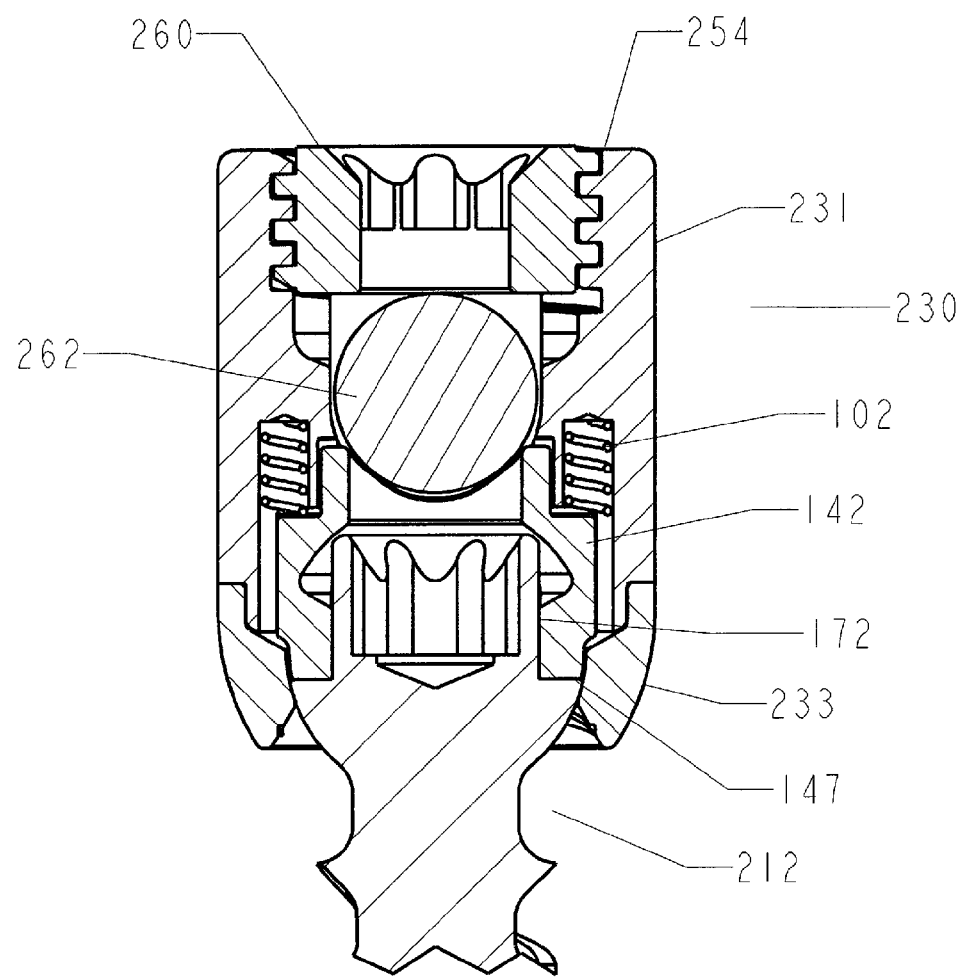
FIG. 35 is a cross section view of the assembled connector for a monoaxial assembly.

As shown in FIG. 35, the U-shaped connector 230 has an upper connector member (231) and a lower connector member (233). A portion of each said side wall is threaded (254) for receipt of a set screw (260) used in securing a rod (262) within the connector. The connector assembly is sized to cooperate with the retaining ring (142) for receipt of various sized rods, as well as limiting the range of motion of between the connector (230) and the screw (212). The screw (212) includes recessed areas for receipt of the retainer ring (142) for limiting the range of motion in a monoaxial direction and with a limit as to displacement by surface (147). Biasing springs (102) place a constant pressure upon the retainer ring which frictionally engages the head of the spherical screw.

Figures 36, 37:
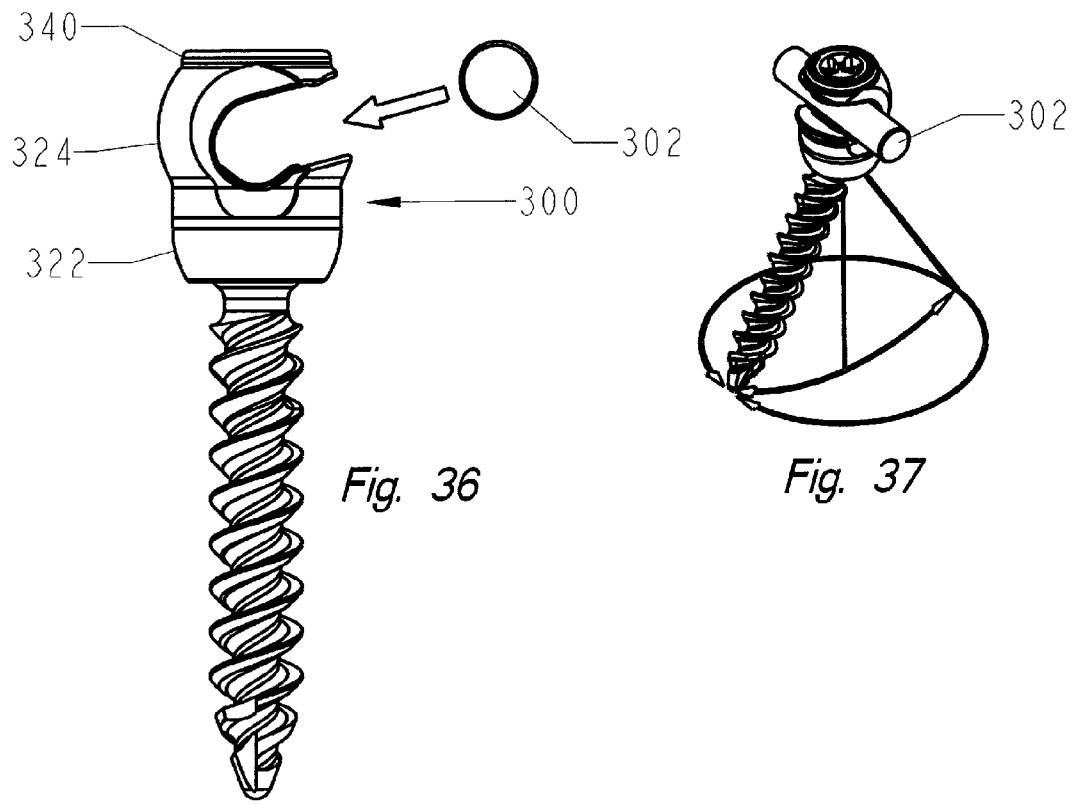
FIG. 36 is a side view of a side loading connector.
FIG. 37 is a pictorial view depicting side loading polyaxial range of motion.
Figure 38:
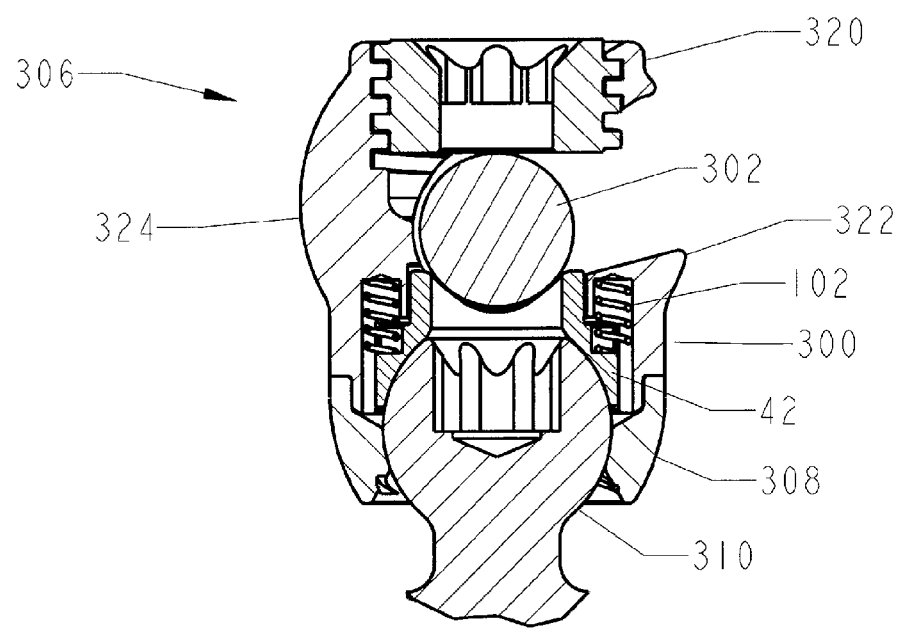
FIG. 38 is a cross sectional side view of a polyaxial side loading connector.
Figure 39:
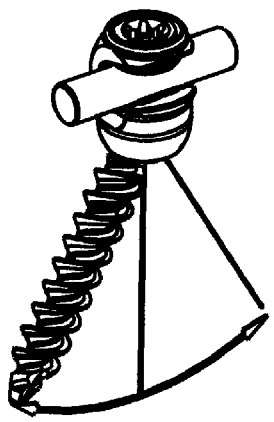
FIG. 39 is a pictorial view depicting side loading monoaxial range of motion.

FIG. 36 is a side view of a side loading connector assembly (300) depicting the placement of rod (302). The insertion of the rod (302) along the side allowing for certain advantages in various surgeries. The strength of the connector has been found to be the same as a top loading connector. FIG. 38 is a cross sectional side view of a polyaxial side loading connector having an upper connector member (306) that is welded to the lower connector member (308) thereby allowing the larger bone screw and spherical head (310) to be placed therein. The upper connector (306) member being generally C shaped having a top annulus portion (320) and a bottom annulus portion (322). The top annulus (320) includes internally directed threads that operatively engage a set screw for securing the rod (302) to the retainer (42) and the spherical head (310). The top annulus portion (320) is formed integrally with the bottom annulus portion (322) and a side wall (324). Side wall (324) circumscribes less than half of the circumference of said top and bottom annulus portions. The retaining ring (42) is again preloaded with the biasing member springs (102) to assist in maintaining the bone screw in position during installation. It should be noted that the removal of the biasing member would not defeat this invention as the biasing member is simply a benefit for the surgeon during installation and the lack of the biasing springs would simply require the holding of the connector while positioning of the connecting rod.

Figure 40:
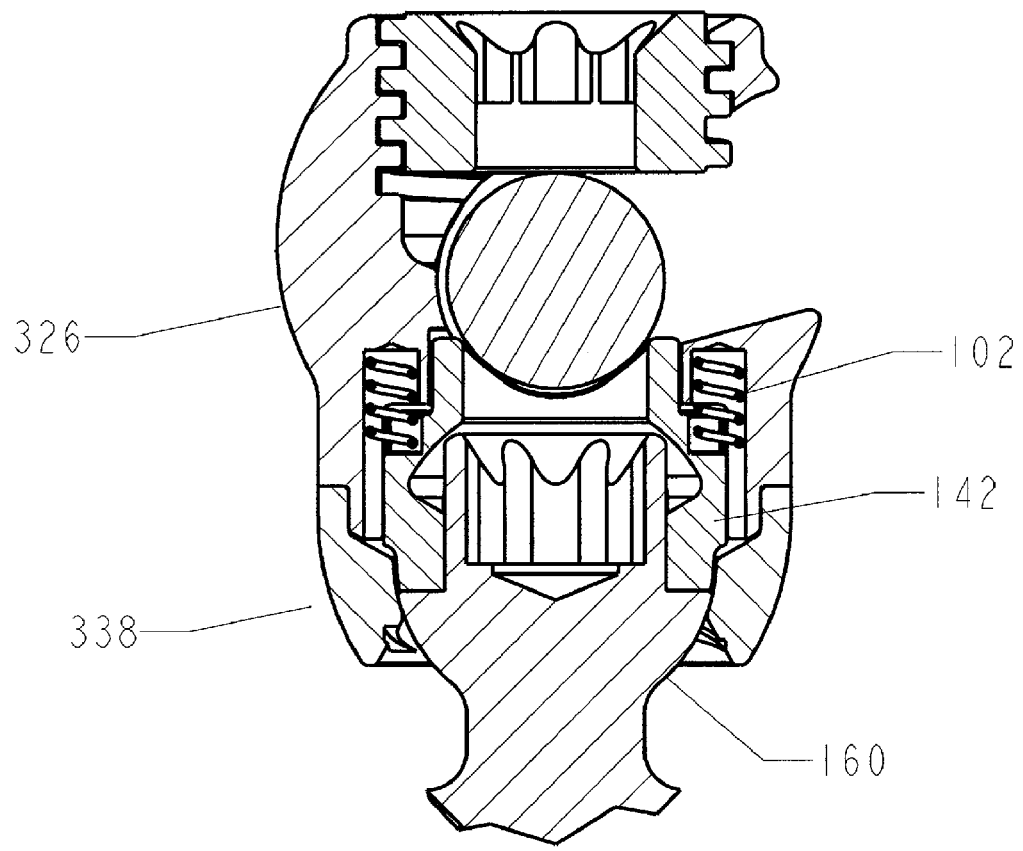
FIG. 40 is a cross sectional side view of a polyaxial side loading connector.

FIG. 40 is a cross sectional side view of a monoaxial side loading connector. In this embodiment the upper body element (326) is again welded to the lower body element (338) thereby allowing the larger bone screw and spherical head (160) to be placed therein. The retaining ring (142) is preloaded with the biasing member springs (102) to assist in maintaining the bone screw in position during installation. The shape of the retainer ring operatively associated with the shape of the recessed area of the bone screw to allow movement only in a monoaxial direction.

It should be noted that while the springs (102) are illustrated as coil springs, any spring or resilient type member suitable for displacing the retaining ring may be utilized without departing from the scope of the invention. Such spring or resilient members may include, but should not be limited to, Belleville type springs, leaf springs, polymeric members and suitable combinations thereof. It should also be noted that the recessed area or the flat portions on the sides of the spherical head may be displaced angularly to provide an assembly that provides a fixed angularly displaced connector or an angularly displaced connector with a limited range of monoaxial movement.

Figure 41:
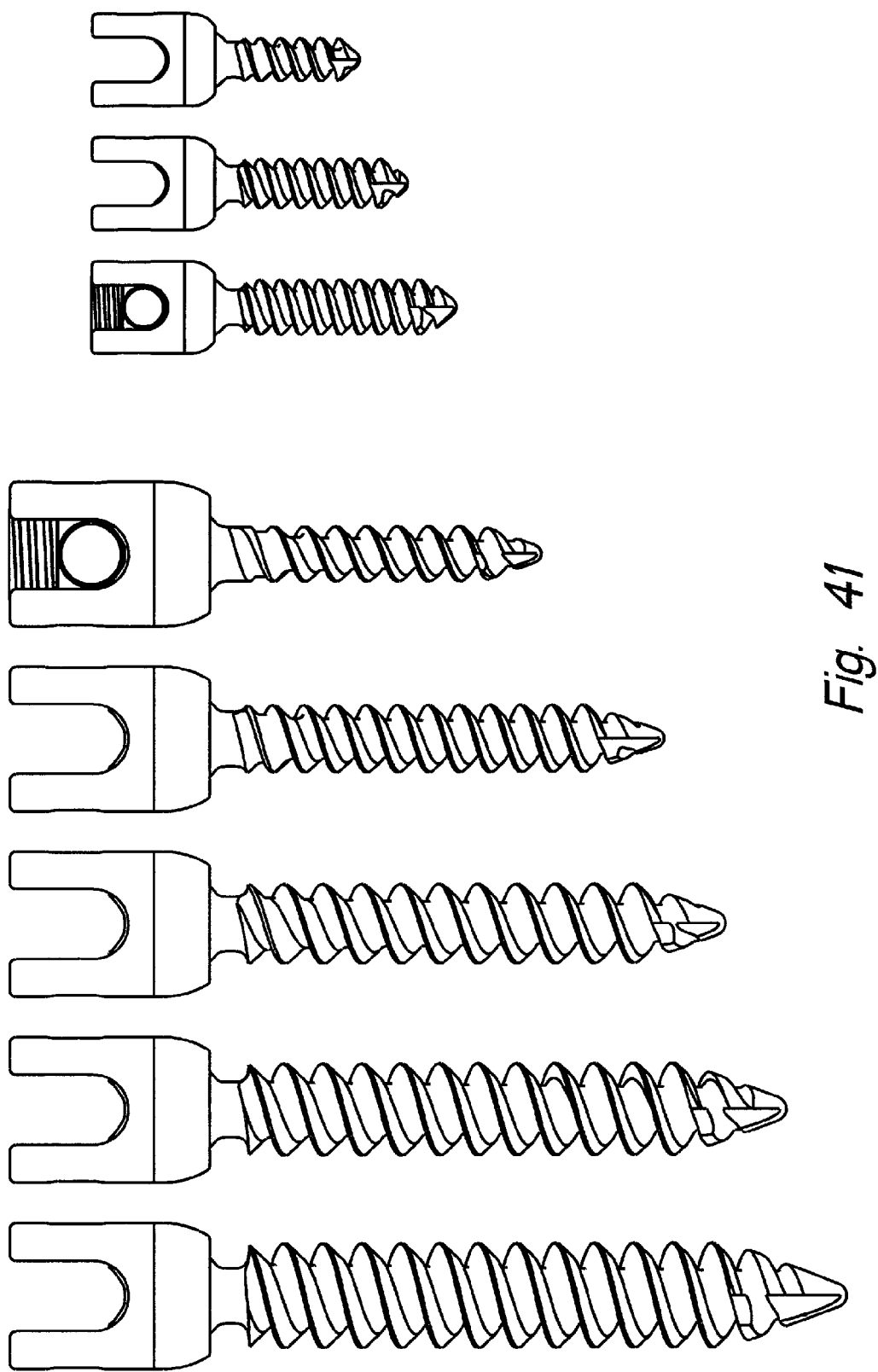
FIG. 41 is a perspective view showing the range of various sized pedicle screws and tulip heads including lumber thoracic spine sizing and cervical-thoracic spine sizing.

FIG. 41 is a perspective view showing the range of various sized pedicle screws and tulip heads including lumber thoracic spine sizing and cervical-thoracic spine sizing. The five larger screws as shown are lumber-thoracic spine sizing. The largest screw is 55 mm and uses an 8.5 mm tulip, the next smaller size screw is 45 mm and uses a 7.5 mm tulip, the next smaller screw is 40 mm and uses a 6.5 mm tulip, the next smaller screw is 35 mm and uses a 5.5 mm tulip and next smaller screw is 25 mm and uses a 4.5 mm tulip. These lumber thoracic screws use a 5.5 mm rod. The three smallest screws as shown are cervical thoracic spine sizing. The largest of this group is 18 mm with a 4.5 mm tulip, the next smaller screw is 14 mm with a 4.0 mm tulip and the smallest screw is 10 mm with a 3.5 mm tulip. These cervical thoracic screws utilize a 3.5 mm rod. The cervical thoracic spine sized screws are approximately two thirds the size of the lumbar thoracic sized screws. With the smaller sized screws the geometric relationship between the screw and the tulip is such that need for threading the screw through the lower member is eliminated. However it has been found that the utilization of at least one groove on the spherical bearing surface seat is very beneficial in gripping and locking the pedicle screws spherical head to the spherical bearing seat.

Figure 42:
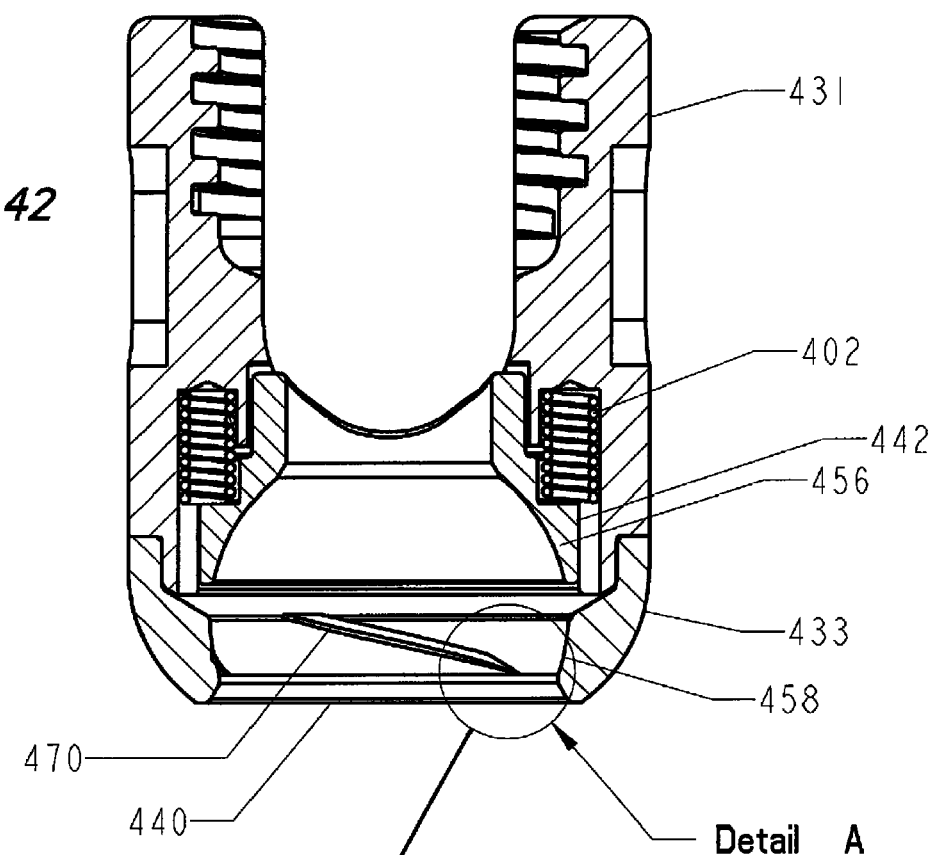
FIG. 42 is a cross sectional view of a polyaxial screw having a groove formed in the spherical seat surface.

The tulip connector assembly shown in FIG. 42 includes an upper connector member 431 and a lower connector member 433. The lower connector member is formed as an annulus and includes an aperture 440. In this configuration the outer diameter of the threaded shank is smaller than the diameter of aperture 440. The lower connector member has a spherical bearing surface 458 that will cooperate with the spherical head 20 on the anchoring screw. The threaded shank is inserted into the lower connector member 433 and through aperture 440. Since the outer diameter of the threaded shank is smaller than the diameter of the aperture 440 the screw will pass through the aperture without the aid of screw threads and the spherical head 20 of the anchoring member can be positioned to cooperate with the spherical bearing seat surface 458 of the lower connector member 433. A retainer ring 442 having a lower spherical surface 456 is resiliently mounted within in a cavity of the upper connector by a biasing member 402 shown in this configuration as a plurality of coil springs. The lower connector member 433 includes spherical seat bearing surface 458. The spherical head of the screw cooperates with spherical bearing surfaces 456 and 458 to permit polyaxial motion of the connector assembly relative to said anchoring member. The upper and lower connector members 431 and 433 are secured to one another using any one of the suitable techniques previously described. This screw can also be used in conjunction with a side loading connector assembly such as that disclosed in FIGS. 36-38. In this instance the upper connector member would be generally C shaped having a top annulus portion and a bottom annulus portion. The top annulus includes internally directed threads that operatively engage a set screw for securing the rod to the retainer and the spherical head. The top annulus portion is formed integrally with the bottom annulus portion and a side wall. Side wall circumscribes less than half of the circumference of said top and bottom annulus portions. Located on spherical bearing seat surface 458 is a gripping and locking groove 470.

Figure 43:
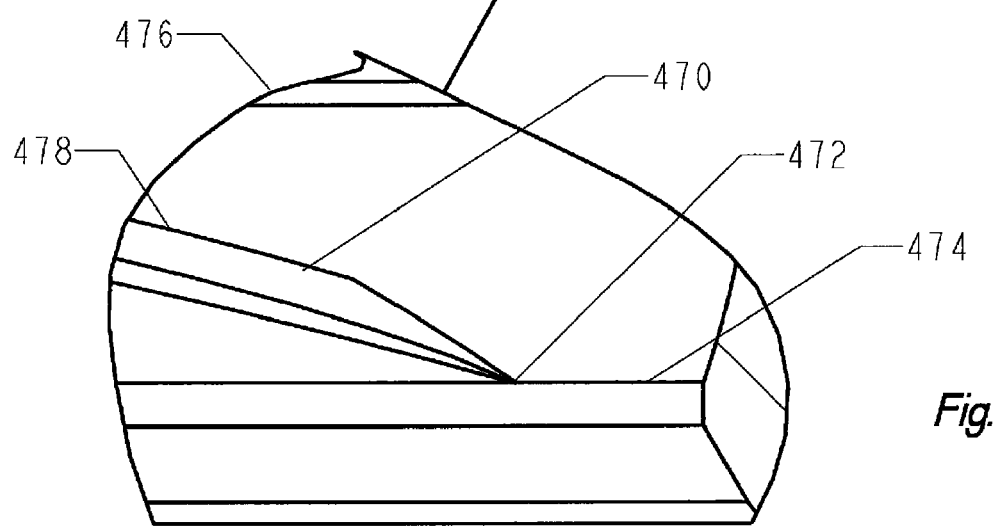
FIG. 43 is an enlarged detailed view of the spherical seat surface shown in FIG. 42 as detail A.

FIG. 43 is an enlarged view of the encircled detail area shown in FIG. 42. The groove 470 circumscribes a minor portion of the circumference of the spherical bearing seat surface 458. The groove 470 starts at a zero depth at a lower portion 474 of the spherical bearing surface 458. The grove 470 penetrates to the design depth as it approaches the upper portion 476 of the spherical bearing seat surface 458. The helical groove 470 is used as an additional aid in locking the spherical head of a screw in its polyaxial position. The groove provides additional points and edges for friction gripping. Under high locking forces the groove also provides a flexing interface for the spherical seat surface to deform and better mate to the spherical head of the screw.

Figure 44:
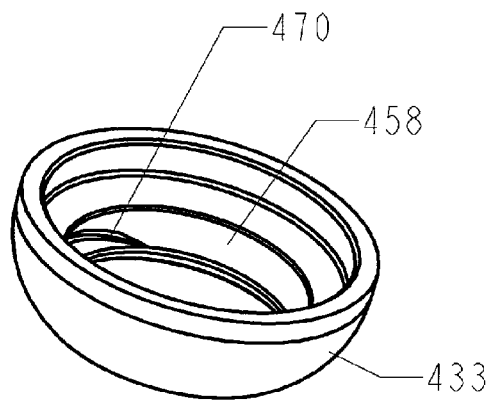
FIG. 44 is a perspective view of the spherical seat surface having a single gripping groove.
Figure 45:
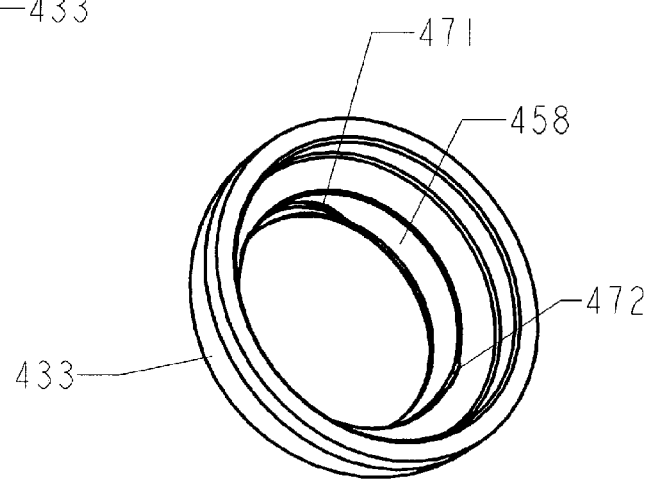
FIG. 45 is a perspective view of the spherical seat surface having two gripping grooves.
Figure 46:
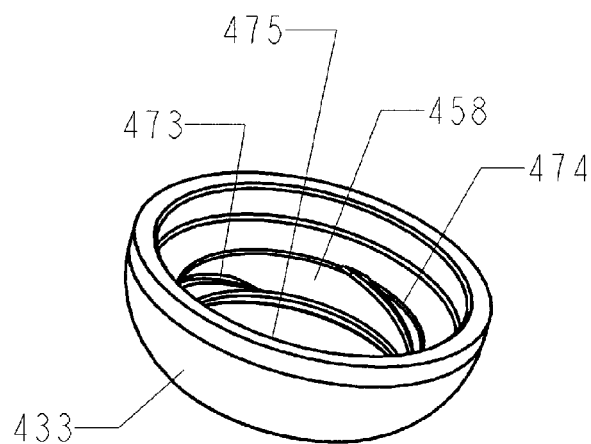
FIGS. 46 and 47 are perspective views of the spherical seat surface having three gripping grooves.
Figure 47:
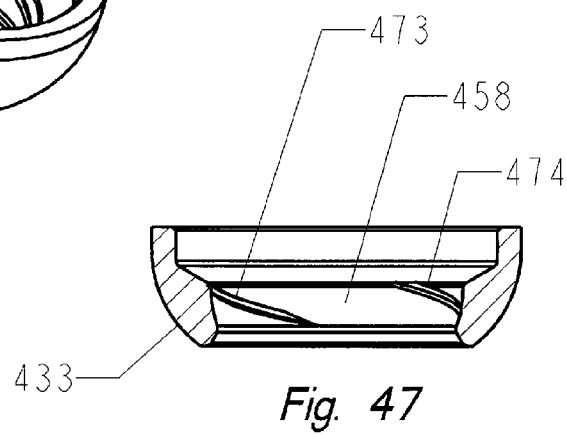

FIG. 44 is a perspective top view of the lower connector member 433 with a single groove 470 on the spherical bearing seat surface 458. FIG. 45 is a perspective top view of an alternative embodiment wherein lower connector member 433 has a pair of grooves 471 and 472 formed on the spherical bearing seat surface 458. FIG. 46 is a perspective top view of a third embodiment wherein the lower connector member 433 includes three grooves 473, 474 and 475 each circumscribing only a minor portion of the bearing seat surface 458. FIG. 47 is a cross sectional view of the embodiment shown in FIG. 46.

Figure 48:
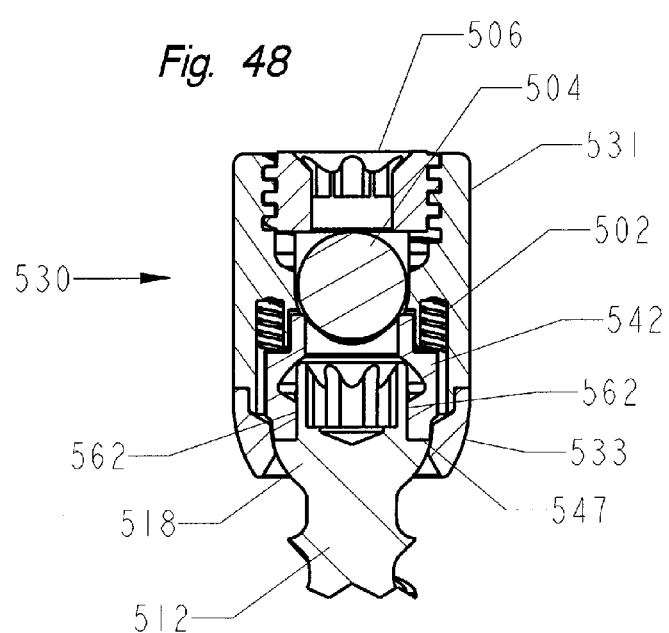
FIG. 48 is a cross sectional view of a monoaxial screw having a spherical seating surface with a gripping groove formed therein.
Figure 50:
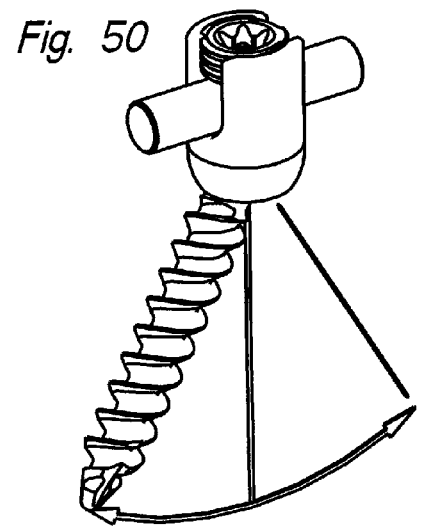
FIG. 50 is a diagrammatic representation of the monoaxial path of the screw shown in FIGS. 47 and 48.
Figure 49:
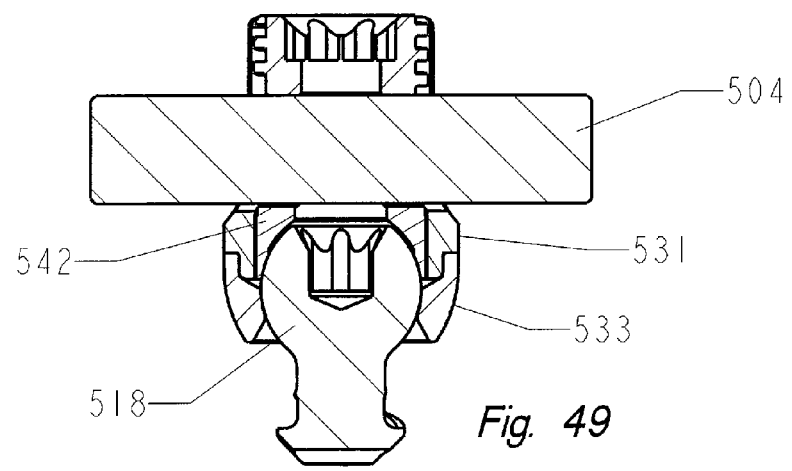
FIG. 49 is a cross sectional view of the screw shown in FIG. 48 rotated ninety degrees.

FIGS. 48 and 49 show different cross sectional views of an embodiment similar to that shown and described in FIG. 42 however in this embodiment the motion of the connector assembly relative to said anchoring member is limited to either mono axial movement or a fixed relative position. The connector assembly (530) has an upper connector member (531) and a lower connector member (533). A portion of each said side wall of the upper connector member is threaded for receipt of a set screw (506) used in securing a rod (504) within the connector assembly (530). The connector assembly (530) is sized to cooperate with the retaining ring (542) for receipt of various sized rods, as well as limiting the range of motion of between the connector assembly (530) and the screw (512). The screw (512) has a spherical connecting head (514). The spherical head includes recessed areas (562) for receipt of the retainer ring (542) for limiting the range of motion in a monoaxial direction and with a limit as to displacement by surfaces (547). Biasing springs (502) place a constant pressure upon the retainer ring (542) which frictionally engages the spherical head (514) of the screw (512). It is also possible to size and configure the recessed areas (562) and retainer surfaces (547) to achieve a fixed relationship between the anchoring screw 512 and the connector assembly (530). The lower connector member 533 includes a spherical bearing seat surface and one, two, or three gripping and locking grooves as illustrated and described in FIGS. 44 through 47.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A pedicle screw comprising:
an anchoring member having a threaded shank and a spherical connector;
a connecting assembly defined by a lower connector member secured to an upper connector member, said lower connector member including a spherical seat surface formed therein, said spherical seat surface having a generally circular aperture sized to allow only said threaded shank of said anchoring member to pass through, said aperture having at least one groove formed on said spherical seat surface sized and configured to grip and lock said spherical connector;

a retainer ring disposed between said lower connector member and said upper connector member, said retainer ring having a lower spherical surface positionable along an upper surface of said spherical connector, said retainer ring constructed and arranged to limit placement of said anchoring member; and a fastener element securable to said upper connector member for engaging of a connection rod member placed within said upper connector member;

wherein when said connecting rod member is placed in said upper connector and said fastener element is secured thereto, the connecting rod member engages said retainer ring and said retainer ring locks said connecting assembly in a fixed position in relation to said anchoring member.

2. The pedicle screw of claim 1, wherein the threaded shank of said anchoring member has an outer diameter that is less than the diameter of said aperture of said spherical seat surface.

3. The pedicle screw of claim 2 wherein said at least one groove in said spherical seat surface is helical.

4. The pedicle screw of claim 3 wherein said spherical seat surface has a lower portion and an upper portion and said at least one helical grove starts at a near zero depth at said lower portion and then increases in depth proximate the upper portion of said spherical seat surface.

5. The pedicle screw of claim 3 wherein said at least one helical groove circumscribes only a portion of the spherical seat surface.

6. The pedicle screw of claim 3 further including a second helical groove that circumscribes only a portion of the spherical seat surface.

7. The pedicle screw of claim 3 further including a second and third groove each circumscribing only a portion of the spherical seat surface.

8. The pedicle screw of claim 1 wherein a lower portion of said retaining ring has a guide surface that is sized and configured to operatively engage an abutment surface within a recess of the spherical connector thereby limiting the range of monoaxial movement of the connector assembly relative to said anchoring member as a function of the shape of the guide surface.

9. The pedicle screw of claim 1 wherein a lower portion of said retaining ring has a guide surface operatively engaged with an abutment surface within a recess of the spherical connector that is sized and configured to thereby limit the range of monoaxial movement of the connector assembly relative to said anchoring member as a function of the shape of the abutment surface.

10. The pedicle screw of claim 1 wherein a lower portion of said retaining ring has a guide surface that is sized and configured to operatively engage an abutment surface within a recess of the spherical connector that also is sized and configured to thereby limit the range of monoaxial movement of the connector assembly relative to said anchoring member as a function of the shape of the abutment surface.

11. The pedicle screw of claim 1 wherein a lower portion of said retaining ring has a guide surface operatively engaged with an abutment surface within a recess of the spherical connector thereby fixing the movement of the connector assembly relative to said anchoring member.

12. The pedicle screw of claim 1 further including at least one biasing member positioned between said retainer ring and said upper connector element.

13. A pedicle screw comprising:

an anchoring member having a shank and a spherical connector;

a connecting assembly defined by a lower connector member secured to an upper connector member, said lower connector member including a spherical seat surface formed therein, said spherical seat surface having a generally circular aperture sized to allow only said threaded shank of said anchoring member to pass through, said aperture having at least one groove formed on said spherical seat surface sized and configured to grip and lock said spherical connector; said upper connector member being generally C shaped having a top annulus portion and a bottom annulus portion, said top annulus portion being connected to said bottom annulus portion with a side wall that circumscribes less than half of the circumference of said top and bottom annulus portions, whereby a connecting rod member can be side loaded into said upper connector member;

a retainer ring disposed between said lower connector member and said upper connector member, said retainer ring having a lower spherical surface positionable along an upper surface of said spherical connector, a fastener element securable to said upper connector member for engaging a connection rod member placed within said upper connector member;

wherein when said connecting rod member is placed in said upper connector and said fastener element is secured thereto, the connecting rod member engages said retainer ring and said retainer ring locks said connecting assembly in a fixed position in relation to said anchoring member.

14. The pedicle screw of claim 13 further including at least one biasing member positioned between said retainer ring and said upper connector element.

15. The pedicle screw of claim 13 wherein a lower portion of said retaining ring has a guide surface that is sized and configured to operatively engage an abutment surface within a recess of the spherical connector thereby limiting the range of monoaxial movement of the connector assembly relative to said anchoring member as a function of the shape of the guide surface.

16. The pedicle screw of claim 13 wherein a lower portion of said retaining ring has a guide surface operatively engaged with an abutment surface within a recess of the spherical connector that is sized and configured to thereby limit the range of monoaxial movement of the connector assembly relative to said anchoring member as a function of the shape of the abutment surface.

17. The pedicle screw of claim 13 wherein a lower portion of said retaining ring has a guide surface that is sized and configured to operatively engage an abutment surface within a recess of the spherical connector that also is sized and configured to thereby limit the range of monoaxial movement of the connector assembly relative to said anchoring member as a function of the shape of the abutment surface.

18. The pedicle screw of claim 13 wherein a lower portion of said retaining ring has a guide surface operatively engaged with an abutment surface within a recess of the spherical connector thereby fixing the movement of the connector assembly relative to said anchoring member.

19. A pedicle screw comprising:

an anchoring member having a threaded shank and a spherical connector;

a connecting assembly defined by a lower connector member secured to an upper connector member, said connector assembly further including a socket for receipt of said spherical connector;

a retainer ring disposed within said socket and between said lower connector member and said upper connector member, said retainer ring having a lower spherical surface positionable along an upper surface of said spherical connector, said retainer ring constructed and arranged to limit placement of said anchoring member; and a fastener element securable to said upper connector member for engaging of a connection rod member placed within said upper connector member said lower connector member including a spherical seat surface formed therein, said spherical seat surface having an aperture and at least one groove formed on said spherical seat surface, the spherical seat surface being sized and configured to grip and lock said spherical connector to said lower connector member; and said upper connector member being generally C shaped having a top annulus portion and a bottom annulus portion, said top annulus portion being connected to said bottom annulus portion with a side wall that circumscribes less than half of the circumference of said top and bottom annulus portions, whereby said connecting rod member can be side loaded into said upper connector member.

20. The pedicle screw of claim 19, wherein the threaded shank of said anchoring member has an outer diameter that is less than the aperture of said spherical seat surface.

21. The pedicle screw of claim 20 wherein said at least one groove in said spherical seat surface is helical.

22. The pedicle screw of claim 21 wherein said spherical seat surface has a lower portion and an upper portion and said at least one helical grove starts at a near zero depth at said lower portion and then increases in depth proximate the upper portion of said spherical seat surface.

23. The pedicle screw of claim 22 wherein said at least one helical groove circumscribes only a portion of the spherical seat surface.

24. The pedicle screw of claim 23 further including a second helical groove that circumscribes only a portion of the spherical seat surface.

25. The pedicle screw of claim 23 further including a second and third groove each circumscribing only a portion of the spherical seat surface.

26. The pedicle screw of claim 19 wherein a lower portion of said retaining ring has a guide surface that is sized and configured to operatively engage an abutment surface within a recess of the spherical connector thereby limiting the range of monoaxial movement of the connector assembly relative to said anchoring member as a function of the shape of the guide surface.

27. The pedicle screw of claim 19 wherein a lower portion of said retaining ring has a guide surface operatively engaged with an abutment surface within a recess of the spherical connector that is sized and configured to thereby limit the range of monoaxial movement of the connector assembly relative to said anchoring member as a function of the shape of the abutment surface.

28. The pedicle screw of claim 19 wherein a lower portion of said retaining ring has a guide surface that is sized and configured to operatively engage an abutment surface within a recess of the spherical connector that also is sized and configured to thereby limit the range of monoaxial movement of the connector assembly relative to said anchoring member as a function of the shape of the abutment surface.

29. The pedicle screw of claim 19 wherein a lower portion of said retaining ring has a guide surface operatively engaged with an abutment surface within a recess of the spherical connector thereby fixing the movement of the connector assembly relative to said anchoring member.

30. The pedicle screw of claim 19 further including at least one biasing member positioned between said retainer ring and said upper connector element.

* * * * *